(12) United States Patent
Plos et al.

(10) Patent No.: US 7,250,064 B2
(45) Date of Patent: Jul. 31, 2007

(54) DYE COMPOSITION COMPRISING AT LEAST ONE FLUORESCENT DYE AND A NON-ASSOCIATIVE THICKENING POLYMER FOR HUMAN KERATIN MATERIALS, PROCESS THEREFOR, AND METHOD THEREOF

(75) Inventors: Grégory Plos, Paris (FR); Luc Gourlaouen, Asnieres (FR)

(73) Assignee: L'Oreal S.A., Paris (FR)

( * ) Notice: Subject to any disclaimer, the term of this patent is extended or adjusted under 35 U.S.C. 154(b) by 202 days.

(21) Appl. No.: 10/814,236

(22) Filed: Apr. 1, 2004

(65) Prior Publication Data
US 2005/0008593 A1 Jan. 13, 2005

Related U.S. Application Data

(60) Provisional application No. 60/468,108, filed on May 6, 2003.

(30) Foreign Application Priority Data
Apr. 1, 2003 (FR) .................................. 03 04028

(51) Int. Cl.
*A61K 7/13* (2006.01)
(52) U.S. Cl. ...................... 8/405; 8/406; 8/407; 8/410; 8/411; 8/421; 8/521; 8/552; 8/648; 132/202; 132/208
(58) Field of Classification Search .................. 8/405, 8/406, 407, 410, 411, 421, 521, 552, 648; 132/202, 208
See application file for complete search history.

(56) References Cited

U.S. PATENT DOCUMENTS

| | | | |
|---|---|---|---|
| 2,261,002 A | 10/1941 | Ritter | |
| 2,271,378 A | 1/1942 | Searle | |
| 2,273,780 A | 2/1942 | Ditmar | |
| 2,375,853 A | 5/1945 | Kirby et al. | |
| 2,388,614 A | 11/1945 | Kirby et al. | |
| 2,454,547 A | 11/1948 | Bock et al. | |
| 2,798,053 A | 7/1957 | Brown | |
| 2,851,424 A | 9/1958 | Switzer et al. | |
| 2,923,692 A | 2/1960 | Ackerman et al. | |
| 2,961,347 A | 11/1960 | Floyd | |
| 2,979,465 A | 4/1961 | Parran et al. | |
| 3,014,041 A | 12/1961 | Hausermann et al. | |
| 3,206,462 A | 9/1965 | McCarty | |
| 3,227,615 A | 1/1966 | Korden | |
| 3,472,840 A | 10/1969 | Stone et al. | |
| 3,632,559 A | 1/1972 | Matter et al. | |
| 3,639,127 A | 2/1972 | Brooker et al. | |
| 3,658,985 A | 4/1972 | Olson, Jr. et al. | |
| 3,856,550 A | 12/1974 | Bens et al. | |
| 3,874,870 A | 4/1975 | Green et al. | |
| 3,910,862 A | 10/1975 | Barabas et al. | |
| 3,912,808 A | 10/1975 | Sokol | |
| 3,915,921 A | 10/1975 | Schlatzer, Jr. | |
| 3,917,817 A | 11/1975 | Vanlerberghe et al. | |
| 3,929,990 A | 12/1975 | Green et al. | |
| 3,966,904 A | 6/1976 | Green et al. | |
| 3,986,825 A | 10/1976 | Sokol | |
| 4,001,432 A | 1/1977 | Green et al. | |
| 4,005,193 A | 1/1977 | Green et al. | |
| 4,013,787 A | 3/1977 | Varlerberghe et al. | |
| 4,025,617 A | 5/1977 | Green et al. | |
| 4,025,627 A | 5/1977 | Green et al. | |
| 4,025,653 A | 5/1977 | Green et al. | |
| 4,026,945 A | 5/1977 | Green et al. | |
| 4,027,020 A | 5/1977 | Green et al. | |
| 4,031,307 A | 6/1977 | DeMartino et al. | |
| 4,075,136 A | 2/1978 | Schaper | |
| 4,131,576 A | 12/1978 | Iovine et al. | |
| 4,157,388 A | 6/1979 | Christiansen | |
| 4,165,367 A | 8/1979 | Chakrabarti | |
| 4,166,894 A | 9/1979 | Schaper | |
| 4,172,887 A | 10/1979 | Vanlerberghe et al. | |
| 4,185,087 A | 1/1980 | Morlino | |
| 4,189,468 A | 2/1980 | Vanlerberghe et al. | |
| 4,197,865 A | 4/1980 | Jacquet et al. | |
| 4,217,914 A | 8/1980 | Jacquet et al. | |
| 4,223,009 A | 9/1980 | Chakrabarti | |
| 4,237,243 A | 12/1980 | Quack et al. | |
| 4,240,450 A | 12/1980 | Grollier et al. | |

(Continued)

FOREIGN PATENT DOCUMENTS

AT 302 534 10/1972

(Continued)

OTHER PUBLICATIONS

English language Derwent Abstract of FR 2 800 612, filed May 11, 2001.

(Continued)

*Primary Examiner*—Eisa Elhilo
(74) *Attorney, Agent, or Firm*—Finnegan, Henderson, Farabow, Garrett & Dunner, LLP

(57) ABSTRACT

The disclosure relates to a composition comprising at least one fluorescent dye and at least one non-associative thickening polymer, to processes using such a composition, and to devices comprising such a composition.

The disclosure also relates to processes and methods for dyeing human keratin materials, for example artificially dyed or pigmented hair and dark skin, with a lightening effect, using compositions comprising at least one fluorescent dye and at least one non-associative thickening polymer.

62 Claims, No Drawings

U.S. PATENT DOCUMENTS

| | | | |
|---|---|---|---|
| 4,256,458 A | 3/1981 | Degen et al. |
| 4,277,581 A | 7/1981 | Vanlerberghe et al. |
| 4,381,919 A | 5/1983 | Jacquet et al. |
| 4,422,853 A | 12/1983 | Jacquet et al. |
| 4,445,521 A | 5/1984 | Grollier et al. |
| 4,509,949 A | 4/1985 | Huang et al. |
| 4,517,174 A | 5/1985 | Jacquet et al. |
| 4,591,610 A | 5/1986 | Grollier |
| 4,608,250 A | 8/1986 | Jacquet et al. |
| 4,693,935 A | 9/1987 | Mazurek |
| 4,702,906 A | 10/1987 | Jacquet et al. |
| 4,719,099 A | 1/1988 | Grollier et al. |
| 4,719,282 A | 1/1988 | Nadolsky et al. |
| 4,728,571 A | 3/1988 | Clemens et al. |
| 4,761,273 A | 8/1988 | Grollier et al. |
| 4,781,724 A | 11/1988 | Wajaroff et al. |
| 4,823,985 A | 4/1989 | Grollier et al. |
| 4,839,166 A | 6/1989 | Grollier et al. |
| 4,948,579 A | 8/1990 | Jacquet et al. |
| 4,961,925 A | 10/1990 | Tsujino et al. |
| 4,972,037 A | 11/1990 | Garbe et al. |
| 4,996,059 A | 2/1991 | Grollier et al. |
| 5,009,880 A | 4/1991 | Grollier et al. |
| 5,057,311 A | 10/1991 | Hanazawa et al. |
| 5,089,252 A | 2/1992 | Grollier et al. |
| 5,139,037 A | 8/1992 | Grollier et al. |
| 5,188,639 A | 2/1993 | Schultz et al. |
| 5,196,189 A | 3/1993 | Jacquet et al. |
| 5,275,808 A | 1/1994 | De Groot et al. |
| 5,316,551 A | 5/1994 | Wenke |
| 5,356,438 A | 10/1994 | Kim et al. |
| 5,445,655 A | 8/1995 | Kuhn et al. |
| 5,635,461 A | 6/1997 | Onitsuka et al. |
| 5,708,151 A | 1/1998 | Möckli |
| 5,733,343 A | 3/1998 | Mockli |
| 5,744,127 A * | 4/1998 | Giuseppe et al. ............ 424/59 |
| 5,792,221 A | 8/1998 | Lagrange et al. |
| 5,830,446 A | 11/1998 | Berthiaume et al. |
| 5,833,997 A | 11/1998 | Mahieu et al. |
| 5,853,708 A | 12/1998 | Cauwet et al. |
| 5,873,494 A | 2/1999 | Dallas, Jr. |
| 5,958,392 A | 9/1999 | Grollier et al. |
| 5,961,667 A | 10/1999 | Doehling et al. |
| 5,962,522 A | 10/1999 | Wacher et al. |
| 6,001,135 A * | 12/1999 | Rondeau et al. ............ 8/407 |
| 6,106,577 A | 8/2000 | Audousset et al. |
| 6,120,780 A | 9/2000 | Dupuis et al. |
| 6,156,077 A | 12/2000 | Shibata et al. |
| 6,180,666 B1 | 1/2001 | Wacher et al. |
| 6,260,556 B1 | 7/2001 | Legrand et al. |
| 6,375,958 B1 | 4/2002 | Cauwet et al. |
| 6,391,062 B1 * | 5/2002 | Vandenbossche et al. ...... 8/405 |
| 6,436,151 B2 | 8/2002 | Cottard et al. |
| 6,436,153 B2 | 8/2002 | Rondeau |
| 6,475,248 B2 | 11/2002 | Ohashi et al. |
| 6,570,019 B2 | 5/2003 | Pasquier et al. |
| 6,576,024 B1 * | 6/2003 | Lang et al. .................. 8/405 |
| 6,592,630 B2 | 7/2003 | Matsunaga et al. |
| 6,616,709 B2 | 9/2003 | Ohashi et al. |
| 6,712,861 B2 | 3/2004 | Rondeau |
| 2001/0010812 A1 | 8/2001 | Chevalier et al. |
| 2001/0023514 A1 | 9/2001 | Cottard et al. |
| 2001/0023515 A1 | 9/2001 | Cottard et al. |
| 2001/0031270 A1 | 10/2001 | Douin et al. |
| 2001/0034914 A1 | 11/2001 | Saunier et al. |
| 2001/0054206 A1 * | 12/2001 | Matsunaga et al. ........... 8/405 |
| 2001/0055580 A1 | 12/2001 | Belli et al. |
| 2002/0004956 A1 | 1/2002 | Rondeau |
| 2002/0012681 A1 | 1/2002 | George et al. |
| 2002/0026676 A1 | 3/2002 | Ohashi et al. |
| 2002/0034489 A1 | 3/2002 | Wiegland et al. |
| 2002/0046431 A1 | 4/2002 | Laurent et al. |
| 2002/0046432 A1 | 4/2002 | Rondeau |
| 2002/0088063 A1 | 7/2002 | Ohashi et al. |
| 2002/0131941 A1 | 9/2002 | Habeck et al. |
| 2002/0176836 A9 | 11/2002 | Belli et al. |
| 2002/0176875 A9 | 11/2002 | Douin et al. |
| 2003/0000023 A9 | 1/2003 | Rondeau |
| 2003/0019052 A1 | 1/2003 | Pratt |
| 2003/0019053 A1 | 1/2003 | Rondeau |
| 2003/0055268 A1 | 3/2003 | Pasquier et al. |
| 2003/0074747 A1 | 4/2003 | Vuarier et al. |
| 2003/0124079 A1 | 7/2003 | Mougin et al. |
| 2003/0131424 A1 | 7/2003 | Audousset et al. |
| 2004/0019981 A1 | 2/2004 | Cottard et al. |
| 2004/0034945 A1 | 2/2004 | Javet et al. |
| 2004/0037796 A1 | 2/2004 | Cottard et al. |
| 2004/0049860 A1 | 3/2004 | Cottard et al. |
| 2004/0105830 A1 | 6/2004 | Boswell et al. |
| 2004/0141943 A1 | 7/2004 | Mougin et al. |
| 2004/0148711 A1 | 8/2004 | Rondeau |
| 2004/0205901 A1 | 10/2004 | Cottard et al. |
| 2004/0258641 A1 | 12/2004 | Plos et al. |
| 2005/0005368 A1 | 1/2005 | Plos et al. |
| 2005/0005369 A1 | 1/2005 | Plos et al. |
| 2005/0008593 A1 | 1/2005 | Plos et al. |
| 2005/0028301 A1 | 2/2005 | Pastore |
| 2005/0144741 A1 | 7/2005 | Lang et al. |

FOREIGN PATENT DOCUMENTS

| | | |
|---|---|---|
| CA | 1 255 603 | 6/1989 |
| CH | 487 231 | 3/1970 |
| DE | 33 133 32 | 10/1994 |
| DE | 196 46 804 A1 | 5/1997 |
| DE | 199 23 438 A1 | 11/2000 |
| DE | 199 26 377 A1 | 12/2000 |
| DE | 100 29 441 A1 | 1/2002 |
| DE | 101 41 683 A1 | 6/2003 |
| DE | 101 48 844 A1 | 10/2003 |
| EP | 0 087 060 B1 | 8/1983 |
| EP | 0 095 238 A2 | 11/1983 |
| EP | 0 080 976 B1 | 9/1986 |
| EP | 0 173 109 | 10/1989 |
| EP | 0 370 470 | 5/1990 |
| EP | 0 412 704 B1 | 2/1991 |
| EP | 0 412 707 B1 | 2/1991 |
| EP | 0 445 342 B1 | 9/1991 |
| EP | 0 486 135 B1 | 5/1992 |
| EP | 0 122 324 B2 | 2/1993 |
| EP | 0 337 354 B1 | 2/1994 |
| EP | 0 582 152 B1 | 2/1994 |
| EP | 0 395 282 | 3/1995 |
| EP | 0 503 853 | 5/1996 |
| EP | 0 714 954 A2 | 6/1996 |
| EP | 0 733 355 A2 | 9/1996 |
| EP | 0 808 150 | 11/1997 |
| EP | 0 815 828 B1 | 6/1999 |
| EP | 0 970 684 A1 | 1/2000 |
| EP | 1 023 891 B1 | 8/2000 |
| EP | 1 099 437 | 5/2001 |
| EP | 1 132 076 A1 | 9/2001 |
| EP | 1 133 977 A2 | 9/2001 |
| EP | 1 191 041 A2 | 3/2002 |
| EP | 1 142 559 B1 | 8/2005 |
| FR | 1492597 | 9/1966 |
| FR | 1583363 | 10/1969 |
| FR | 2077143 | 10/1971 |
| FR | 2080759 | 11/1971 |
| FR | 2103210 | 7/1972 |
| FR | 2162025 | 7/1973 |
| FR | 2190406 | 2/1974 |
| FR | 2252840 | 6/1975 |
| FR | 2270846 | 12/1975 |

| | | |
|---|---|---|
| FR | 2280361 | 2/1976 |
| FR | 2316271 | 1/1977 |
| FR | 2320330 | 3/1977 |
| FR | 2336434 | 7/1977 |
| FR | 2368508 | 5/1978 |
| FR | 2383660 | 10/1978 |
| FR | 2393573 | 1/1979 |
| FR | 2411219 | 7/1979 |
| FR | 2416723 | 9/1979 |
| FR | 2470596 | 6/1981 |
| FR | 2505348 | 11/1982 |
| FR | 2519863 | 7/1983 |
| FR | 2542997 | 9/1984 |
| FR | 2586913 | 3/1987 |
| FR | 2589476 | 5/1987 |
| FR | 2598611 | 11/1987 |
| FR | 2692572 | 6/1992 |
| FR | 2741261 | 5/1997 |
| FR | 2 773 470 | 7/1999 |
| FR | 2 797 877 | 3/2001 |
| FR | 2 800 612 | 5/2001 |
| FR | 2811993 | 1/2002 |
| FR | 2820032 | 8/2002 |
| FR | 2830189 | 4/2003 |
| GB | 746864 | 3/1956 |
| GB | 759385 | 10/1956 |
| GB | 1214394 | 1/1970 |
| GB | 1546809 | 5/1979 |
| GB | 1554331 | 10/1979 |
| JP | 48-17362 | 5/1973 |
| JP | 54-86521 | 7/1979 |
| JP | 2-200612 | 8/1990 |
| JP | 6-128128 | 5/1994 |
| JP | 6-183935 | 7/1994 |
| JP | 6-227954 | 8/1994 |
| JP | 8-183716 | 7/1996 |
| JP | 8-208448 | 8/1996 |
| JP | 8-259426 | 10/1996 |
| JP | 9-183714 | 7/1997 |
| JP | 10-236929 | 9/1998 |
| JP | 11-021214 | 1/1999 |
| JP | 11-60453 | 3/1999 |
| JP | 11-343218 | 12/1999 |
| JP | 2000-01417 | 1/2000 |
| JP | 2000-86472 | 3/2000 |
| JP | 2000-505841 | 5/2000 |
| JP | 2001-172120 | 6/2001 |
| JP | 2001-220330 | 8/2001 |
| JP | 2001-226217 | 8/2001 |
| JP | 2001-261534 | 9/2001 |
| JP | 2001-261536 | 9/2001 |
| JP | 2001-294519 | 10/2001 |
| JP | 2001-302473 | 10/2001 |
| JP | 2001-516701 | 10/2001 |
| JP | 2001-516705 | 10/2001 |
| JP | 2001-516706 | 10/2001 |
| JP | 2001-516707 | 10/2001 |
| JP | 2002-12523 | 1/2002 |
| JP | 2002-12530 | 1/2002 |
| JP | 2002-47151 | 2/2002 |
| JP | 2002-226338 | 8/2002 |
| JP | 2002-249419 | 9/2002 |
| JP | 2002-326911 | 11/2002 |
| JP | 2003-55177 | 2/2003 |
| JP | 2004-059468 | 2/2004 |
| JP | 2004-307494 | 11/2004 |
| JP | 2004 307495 | 11/2004 |
| WO | WO 93/11103 | 6/1993 |
| WO | WO 93/23009 | 11/1993 |
| WO | WO 93/23446 | 11/1993 |
| WO | WO 94/02022 | 2/1994 |
| WO | WO 95/00578 | 1/1995 |
| WO | WO 95/01772 | 1/1995 |
| WO | WO 95/15144 | 6/1995 |
| WO | WO 97/18795 | 5/1997 |
| WO | WO 99/12846 | 3/1999 |
| WO | WO 99/13822 | 3/1999 |
| WO | WO 99/13823 | 3/1999 |
| WO | WO 99/13824 | 3/1999 |
| WO | WO 99/13828 | 3/1999 |
| WO | WO 99/13841 | 3/1999 |
| WO | WO 99/13844 | 3/1999 |
| WO | WO 99/13845 | 3/1999 |
| WO | WO 99/13846 | 3/1999 |
| WO | WO 99/13847 | 3/1999 |
| WO | WO 99/13849 | 3/1999 |
| WO | WO 99/20235 A1 | 4/1999 |
| WO | WO 99/36045 * | 7/1999 |
| WO | WO 00/68282 | 11/2000 |
| WO | WO 00/71085 A2 | 11/2000 |
| WO | WO 01/43714 | 6/2001 |
| WO | WO 01/62759 A1 | 8/2001 |
| WO | WO 01/78669 | 10/2001 |
| WO | WO 02/32386 A2 | 4/2002 |
| WO | WO 02/38115 A1 | 5/2002 |
| WO | WO 02/39964 A1 | 5/2002 |
| WO | WO 02/45673 A2 | 6/2002 |
| WO | WO 02/058646 A1 | 8/2002 |
| WO | WO 02/058647 A1 | 8/2002 |
| WO | WO 02/074270 | 9/2002 |
| WO | WO 03/022232 A2 | 3/2003 |
| WO | WO 03/028685 A1 | 4/2003 |
| WO | WO 03/029359 | 4/2003 |

OTHER PUBLICATIONS

CAS Abstract for JP 2000-136340—Chemical Abstracts Service; Database Accession No. 2000: 317079; XP-002269220, JP 2000136340 (Pentel Co., Ltd.), May 16, 2000.
Co-pending U.S. Appl. No. 10/814,333, filed Apr. 1, 2004.
Co-pending U.S. Appl. No. 10/814,334, filed Apr. 1, 2004.
Co-pending U.S. Appl. No. 10/814,430, filed Apr. 1, 2004.
Co-pending U.S. Appl. No. 10/814,305, filed Apr. 1, 2004.
Co-pending U.S. Appl. No. 10/814,335, filed Apr. 1, 2004.
Co-pending U.S. Appl. No. 10/814,428, filed Apr. 1, 2004.
Co-pending U.S. Appl. No. 10/490,869, filed Apr. 1, 2004.
Co-pending U.S. Appl. No. 10/814,300, filed Apr. 1, 2004.
Co-pending U.S. Appl. No. 10/814,338, filed Apr. 1, 2004.
Co-pending U.S. Appl. No. 10/814,337, filed Apr. 1, 2004.
Co-pending U.S. Appl. No. 10/814,585, filed Apr. 1, 2004.
Co-pending U.S. Appl. No. 10/742,995, filed Apr. 1, 2004.
Co-pending U.S. Appl. No. 10/814,336, filed Apr. 1, 2004.
English Language Derwent Abstract of DE 33 133 32.
English Language Derwent Abstract of DE 100 29 441.
English Language Derwent Abstract of DE 101 41 683.
English Language Derwent Abstract of DE 101 48 844.
English Language Derwent Abstract of DE 199 23 438.
English Language Derwent Abstract of DE 199 26 377.
English Language Derwent Abstract of EP 0 080 976.
English Language Derwent Abstract of EP 0 087 060.
English Language Derwent Abstract of EP 1 023 891.
English Language Derwent Abstract of EP 1 099 437.
English Language Derwent Abstract of FR 2 773 470.
English Language Derwent Abstract of FR 2,797,877.
English Language Abstract of FR 2 589 476 (EP 0 225 261) from EPO website.
English Language Abstract of JP 9-183714.
English Language Derwent Abstract of JP 10-236929.
English Language Derwent Abstract of JP 11-060453.
English Language Derwent Abstract of JP 11-21214.
English Language Derwent Abstract of JP 2000-1417.
English Language Derwent Abstract of JP 2000-086472.
English Language Derwent Abstract of JP 2001-172120.
English Language Derwent Abstract of JP 2001-261534.
English Language Abstract of JP 2001-294519 from Japio database.
English Language Abstract of JP 2001-302473.

English Language JPO Abstract Abstract of JP 2002-47151.
English Language Derwent Abstract of JP 2001-516701.
English Language Derwent Abstract of JP 2001-516706.
English Language Derwent Abstract of JP 2001-516707.
English Language Derwent Abstract of JP 2002-226338.
English Language Abstract of JP 2002-249419 from Japio database.
English Language Abstract of JP 2002-326911.
English Language Derwent Abstract of JP 2004-59468.
English Language Derwent Abstract of JP 2-200612.
English Language Derwent Abstract of JP 6-183935.
English Language Derwent Abstract of JP 6-227954.
English Language Derwent Abstract of JP 8-183716.
English Language Derwent Abstract of JP 8-208448.
English Language Derwent Abstract of WO 02/32386.
French Search Report for French Patent Application No. FR 02/16669, priority document for co-pending U.S. Appl. No. 10/742,995, Aug. 6, 2003.
French Search Report for French Patent Application No. FR 03/04021, priority document for U.S. Appl. No. 10/814,337, Dec. 8, 2003.
French Search Report for French Patent Application No. FR 03/04022, priority document for co-pending U.S. Appl. No. 10/814,336, Nov. 20, 2003.
French Search Report for French Patent Application No. FR 03/04024, priority document for co-pending U.S. Appl. No. 10/814,585, Dec. 8, 2003.
French Search Report for French Patent Application No. FR 03/04026, priority document for co-pending U.S. Appl. No. 10/814,335, Nov. 21, 2003.
French Search Report for French Patent Application No. FR 03/04027, priority document for co-pending U.S. Appl. No. 10/814,428, Nov. 28, 2003.
French Search Report for French Patent Application No. FR 03/04028, priority document for co-pending U.S. Appl. No. 10/814,236, Nov. 25, 2003. (present case).
French Search Report for French Patent Application No. FR 03/04029, priority document for co-pending U.S. Appl. No. 10/814,430, Feb. 5, 2004.
French Search Report for French Patent Application No. FR 03/04030, priority document for co-pending U.S. Appl. No. 10/814,300, Nov. 27, 2003.
French Search Report for French Patent Application No. FR 03/04031, priority document for co-pending U.S. Appl. No. 10/814,333, Jan. 8, 2004.
French Search Report for French Patent Application No. FR 03/04033, priority document for co-pending U.S. Appl. No. 10/814,334, Nov. 28, 2003.
French Search Report for French Patent Application No. FR 03/04034, priority document for co-pending U.S. Appl. No. 10/814,338, Feb. 17, 2004.
French Search Report for French Patent Application No. FR 03/04035, priority document for co-pending U.S. Appl. No. 10/814,305, Feb. 5, 2004.
International Search Report for PCT Application No. PCT/FR 02/03252, (for co-pending U.S. Appl. No. 10/490,869, Jan. 20, 2003.
Office Action mailed Nov. 17, 2005 in co-pending U.S. Appl. No. 10/814,336.
Office Action mailed Nov. 3, 2005 in co-pending U.S. Appl. No. 10/490,869.
Office Action mailed May 26, 2006 in co-pending U.S. Appl. No. 10/490,869.
Office Action mailed Nov. 2, 2005 in co-pending U.S. Appl. No. 10/814,338.
Office Action mailed May 30, 2006 in co-pending U.S. Appl. No. 10/814,338.
Office Action mailed Nov. 2, 2005 in co-pending U.S. Appl. No. 10/742,995.
Office Action mailed May 18, 2006 in co-pending U.S. Appl. No. 10/814,333.
Office Action mailed Mar. 27, 2006 in co-pending U.S. Appl. No. 10/814,334.
Office Action mailed Jun. 8, 2006 in co-pending U.S. Appl. No. 10/814,430.
Office Action mailed Mar. 15, 2006 in co-pending U.S. Appl. No. 10/814,305.
Office Action mailed Mar. 23, 2006 in co-pending U.S. Appl. No. 10/814,300.
Office Action mailed May 25, 2006 in co-pending U.S. Appl. No. 10/814,335.
Office Action mailed Mar. 15, 2006 in co-pending U.S. Appl. No. 10/814,337.
Jacobi, Otto and Jacobi, Gertrud, "Investigation into the reciprocal action of cosmetics and the biosphere of the stratum corneum of the skin," *Cosmetics and Toiletries*, 91:25-32 (Jan. 1976).
Science Des Traitements Capillaires [Hair Treatment Sciences] by Charles Zviak, 1988, published by Masson, pp. 215 and 278.
M. Schlossmann, "The Chemistry and Manufacture of Cosmetics Formulating," 2(3):522-526 (2000).
D.F. Williams et al., "Chemistry and Technology of the Cosmetics and Toiletries Industry," ed. 2, pp. 77-78 (1996).
Yuuki Kagoubutsu Jilen (Dictionary of Organic Compounds), Kodansha Ltd., Aug. 10, 2002, p. 908.
G. Fonnum, J. Bakke and Fk. Hansen—Colloid Polym. Sci. 271:380-389 (1993).
Zviak, C., The Science of Hair Care, pp. 215 and 278 (1986).
Mishra, J.K. et al. "Synthesis of some bischromophoric dyes containing nonabsorbing flexible bridge," Indian Journal of Chemistry, vol. 31B, pp. 118-122, Feb. 1992.
Office Action mailed Apr. 6, 2006 in co-pending U.S. Appl. No. 10/742,995.
Office Action mailed Aug. 24, 2006 in co-pending U.S. Appl. No. 10/814,305.
Office Action mailed Aug. 28, 2006 in co-pending U.S. Appl. No. 10/814,300.
Office Action mailed Jan. 25, 2007 in co-pending U.S. Appl. No. 10/814,336.
Office Action mailed Jul. 7, 2006, in co-pending U.S. Appl. No. 10/814,585.
Office Action mailed Jun. 21, 2006, in co-pending U.S. Appl. No. 10/814,336.
Office Action mailed Oct. 23, 2006 in co-pending U.S. Appl. No. 10/742,995.

\* cited by examiner

DYE COMPOSITION COMPRISING AT LEAST ONE FLUORESCENT DYE AND A NON-ASSOCIATIVE THICKENING POLYMER FOR HUMAN KERATIN MATERIALS, PROCESS THEREFOR, AND METHOD THEREOF

This application claims benefit of U.S. Provisional Application No. 60/468,108, filed May 6, 2003.

The present disclosure relates to a composition comprising at least one fluorescent dye and at least one non-associative thickening polymer. The present disclosure also relates to the process and the device using these compositions and to the use of these compositions for dyeing, with a lightening effect, human keratin materials, such as keratin fibers that are artificially dyed or pigmented, and in another embodiment, dark skin.

It is common for individuals with dark skin to wish to lighten their skin and for this purpose to use cosmetic or dermatological compositions comprising bleaching agents.

The substances most commonly used as bleaching agents are hydroquinone and its derivatives, kojic acid and its derivatives, azelaic acid, arbutin and its derivatives, alone or in combination with other active agents.

However, these agents are not without their drawbacks. For example, they need to be used for a long time and in large amounts in order to obtain a bleaching effect on the skin. No immediate effect can be observed on applying compositions comprising them.

In addition, hydroquinone and its derivatives may be used in an amount that is effective to produce a visible bleaching effect. For example, hydroquinone is known for its cytotoxicity towards melanocyte.

Moreover, kojic acid and its derivatives have the drawback of being expensive and consequently of not being able to be used in large amounts in products for commercial mass distribution.

There is thus still a need in the art for cosmetic compositions that allow a lighter, uniform, homogeneous skin tone of natural appearance to be obtained, these compositions may also have satisfactory transparency after application to the skin.

In the field of haircare, mention may be made of two major types of hair dyeing.

The first is semi-permanent dyeing or direct dyeing, which uses dyes capable of giving the hair's natural color a more or less pronounced modification that can withstand shampooing several times. These dyes may also be referred to as direct dyes and may be used in two different ways. The colorations may be performed by applying the composition comprising the direct dye(s) directly to the keratin fibers, or by applying a mixture, prepared extemporaneously, of a composition comprising the direct dye(s) with a composition comprising an oxidizing bleaching agent, for example, an aqueous hydrogen peroxide solution. Such a process may be referred to as "lightening direct dyeing."

The second major type of hair dyeing is permanent dyeing or oxidation dyeing. This may be performed with "oxidation" dye precursors, which are colorless or weakly colored compounds which, once mixed with oxidizing products, at the time of use, can give rise to colored compounds and dyes via a process of oxidative condensation. It is often necessary to combine one or more direct dyes with the oxidation bases and couplers in order to neutralize or attenuate the shades with too much of a red, orange or golden glint or, alternatively, to accentuate these red, orange, or golden glints.

Among the available direct dyes, nitrobenzene direct dyes are not sufficiently strong, and indoamines, quinone dyes, and natural dyes have low affinity for keratin fibers and consequently may lead to colorations that are not sufficiently fast with respect to the various treatments to which the fibers may be subjected, such as shampooing.

In addition, there is a need in the art to obtain a lightening effect on human keratin fibers. This lightening may be obtained via a process of bleaching the melanins of the hair via an oxidizing system comprising hydrogen peroxide optionally combined with persalts. This bleaching system has the drawback of degrading the keratin fibers and of impairing their cosmetic properties.

One aspect of the present disclosure is to solve at least one of the drawbacks of the prior art. In another aspect, the present disclosure proposes a composition that has good dyeing affinity for keratin materials such as keratin fibers, good resistance properties with respect to external agents, such as those encountered when shampooing, and that also make it possible to obtain lightening without impairing the treated material, such as the keratin fiber.

The present inventors have found that the use of fluorescent dyes, such as those in the orange range, in the presence of non-associative thickeners, may avoid one or more of the drawbacks of the prior art.

Thus, disclosed herein is a composition comprising, in a cosmetically acceptable medium, at least one fluorescent dye that is soluble in said medium and at least one non-associative thickening polymer chosen from the group comprising:

(i) crosslinked acrylic acid homopolymers;
(ii) crosslinked 2-acrylamido-2-methylpropanesulphonic acid homopolymers and the partially or totally neutralized acrylamide crosslinked copolymers thereof;
(iii) ammonium acrylate homopolymers or copolymers of ammonium acrylate and of acrylamide;
(iv) dimethylaminoethyl methacrylate homopolymers quaternized with methyl chloride; and copolymers of dimethylaminoethyl methacrylate quaternized with methyl chloride and of acrylamide;
(v) nonionic guar gums;
(vi) biopolysaccharide gums of microbial origin, such as scleroglucan gum or xanthan gum;
(vii) gums derived from plant exudates, such as gum arabic, ghatti gum, karaya gum and gum tragacanth;
(viii) hydroxypropyl or carboxymethyl celluloses;
(ix) pectins; and
(x) alginates;.

wherein the composition does not comprise, as the at least one fluorescent dye, 2-[2-(4-dialkylamino)phenylethenyl]-1-alkylpyridinium wherein the alkyl radical of the pyridinium nucleus represents a methyl or ethyl radical, the alkyl radical of the benzene nucleus represents a methyl radical and wherein the counterion is a halide.

Also disclosed herein is a process for dyeing human keratin fibers with a lightening effect, wherein the following steps are performed:

a) a composition according to the present disclosure is applied to said fibers, for a time that is sufficient to develop the desired coloration and lightening,
b) the fibers are optionally rinsed,
c) the fibers are optionally washed with shampoo and rinsed,
d) the fibers are dried or are left to dry.

Further disclosed herein is a process for coloring dark skin with a lightening effect, in which the composition according to the present disclosure is applied to the skin and the skin is then dried or allowed to dry.

Another subject of the present disclosure is, a process for dyeing human keratin materials with a lightening effect, with a composition comprising, in a cosmetically acceptable medium, at least one fluorescent dye that is soluble in said medium and at least one non-associative thickening polymer chosen from the group comprising:

(i) crosslinked acrylic acid homopolymers;
(ii) crosslinked 2-acrylamido-2-methylpropanesulphonic acid homopolymers and the partially or totally neutralized acrylamide crosslinked copolymers thereof;
(iii) ammonium acrylate homopolymers or copolymers of ammonium acrylate and of acrylamide;
(iv) dimethylaminoethyl methacrylate homopolymers quaternized with methyl chloride; and copolymers of dimethylaminoethyl methacrylate quaternized with methyl chloride and of acrylamide;
(v) nonionic guar gums;
(vi) biopolysaccharide gums of microbial origin, such as scleroglucan gum or xanthan gum;
(vii) gums derived from plant exudates, such as gum arabic, ghatti gum, karaya gum and gum tragacanth;
(viii) hydroxypropyl or preferably carboxymethyl celluloses;
(ix) pectins; and
(x) alginates.

Also disclosed herein is a multi-compartment device for dyeing and lightening human keratin fibers, comprising at least one compartment comprising the composition according to the present disclosure, and at least one other compartment comprising a composition comprising at least one oxidizing agent.

The compositions of the present disclosure may also allow better fixing of the fluorescent dye onto the keratin materials, which may be reflected by an increased fluorescent effect and a lightening effect that is greater than that obtained with the fluorescent dye used alone.

Better resistance of the result with respect to washing or shampooing may also be found.

Other characteristics and advantages of the present disclosure will emerge more clearly on reading the description and the examples that follow.

Unless otherwise indicated, the limits of the ranges of values that are given in the description are included in these ranges.

As mentioned previously, the composition according to the present disclosure comprises at least one fluorescent dye and at least one non-associative thickening polymer.

For the purposes of the present disclosure, the term "non-associative thickening polymers" means thickening polymers not comprising $C_{10}$-$C_{30}$ fatty chains.

For example, a first family (i) of non-associative thickening polymers that is suitable is represented by crosslinked acrylic acid homopolymers.

Among the homopolymers of this type, non-limiting mention may be made of those crosslinked with an allylic alcohol ether of the sugar series, for instance the products sold under the names Carbopols 980, 981, 954, 2984, and 5984 by the company Noveon or the products sold under the names Synthalen M and Synthalen K by the company 3 VSA.

With regard to the non-associative thickening polymers of a second family (ii), i.e. the crosslinked 2-acrylamido-2-methylpropanesulphonic acid homopolymers and the partially or totally neutralized acrylamide crosslinked copolymers thereof, non-limiting mention may be made of the homopolymers described in Patent Application EP 815,828, to which reference may be made in this respect. Among the partially or totally neutralized crosslinked copolymers of 2-acrylamido-2-methylpropanesulphonic acid and of acrylamide, non-limiting mention may be made of the product described in Example 1 of publication EP 503,853, and reference may be made to said document as regards these polymers. It may also be noted that, in the case where the compounds are neutralized, they may be neutralized by using a base such as sodium hydroxide, potassium hydroxide, or an amine.

A third family (iii) of non-associative thickening polymers is represented by ammonium acrylate homopolymers or copolymers of ammonium acrylate and of acrylamide.

Non-limiting examples of ammonium acrylate homopolymers that may be mentioned include the product sold under the name Microsap PAS 5193 by the company Hoechst. Among the copolymers of ammonium acrylate and of acrylamide, non-limiting mention may be made of the product sold under the name Bozepol C Nouveau or the product PAS 5193 sold by the company Hoechst. Non-limiting reference may also be made to Pat. No. FR 2,416,723, and U.S. Pat. Nos. 2,798,053 and 2,923,692 with respect to the description and the preparation of such compounds.

In another embodiment, the dimethylaminoethyl methacrylate homopolymers quaternized with methyl chloride or the copolymers of dimethylaminoethyl methacrylate quaternized with methyl chloride and of acrylamide comprise another family (iv) of polymers that may be suitable for implementing the present disclosure.

Among the homopolymers of this family (iv), non-limiting mention may be made of the products sold under the names Salcare 95 and Salcare 96 by the company Ciba-Allied Colloids. Among the copolymers of this family, non-limiting mention may also be made of the product Salcare SC92 sold by Ciba-Allied Colloids or the product PAS 5194 sold by Hoechst. These polymers are described, for example in publication EP 395,282, to which reference may be made regarding these polymers.

In yet another example, with regards the nonionic guar gums (family (v)), non-limiting mention may be made of unmodified nonionic guar gums sold under the name Vidogum GH 175 by the company Unipectine, and under the name Jaguar C by the company Meyhall.

According to another aspect of the present disclosure, the nonionic guar gums that may be used according to the present disclosure may be modified with $C_1$-$C_6$ hydroxyalkyl groups.

Among the hydroxyalkyl groups, non-limiting mention may be made of hydroxymethyl, hydroxyethyl, hydroxypropyl, and hydroxybutyl groups.

These guar gums are well known in the prior art and may be prepared, for example, by reacting corresponding alkene oxides, for example propylene oxides, with guar gum, so as to obtain a guar gum modified with hydroxypropyl groups.

The degree of hydroxyalkylation, which corresponds to the number of alkylene oxide molecules consumed by the number of free hydroxyl functions present on the guar gum, may range, for example, from 0.4 to 1.2.

For example, such nonionic-guar gums optionally modified with hydroxyalkyl groups may be found under the trade names Jaguar HP8, Jaguar HP60, Jaguar HP120, Jaguar DC 293, and Jaguar HP 105 by the company Meyhall, or under the name Galactasol 4H4FD2 by the company Aqualon.

The biopolysaccharide gums of microbial origin (family (vi)), such as scleroglucan gum or xanthan gum; the gums derived from plant exudates (family (vii)), such as gum arabic, ghatti gum, karaya gum, and gum tragacanth; the hydroxypropyl or carboxymethyl celluloses (family (viii)); the pectins (family (ix)); and the alginates (x) are well known to those skilled in the art and are described, for example, in the book by Robert L. Davidson entitled "*Handbook of Water-soluble Gums and Resins*" published by Mc Graw Hill Book Company (1980), which is incorporated herein with respect to the above mentioned compounds.

The non-associative thickening polymers used in the context of the present disclosure may be used, for example, in an amount from 0.01% to 10% by weight relative to the total weight of the composition applied to the fibers. In another example, this amount may range from 0.1% to 5% by weight relative to the total weight of the composition.

The fluorescent dye is one of the other constituent components of the composition according to the present disclosure.

For the purposes of the present disclosure, the term "fluorescent dye" means a dye which is a molecule that colors by itself, and thus absorbs light in the visible spectrum (wavelengths ranging from 360 to 760 nanometers) and possibly in the ultraviolet spectrum, but which, in contrast with a standard dye, converts the absorbed energy into fluorescent light of a longer wavelength emitted in the visible region of the spectrum.

A fluorescent dye according to the present disclosure may be differentiated from an optical brightener. Optical brighteners, which may also be known as brighteners, fluorescent brighteners, fluorescent brightening agents, fluorescent whitening agents, whiteners or fluorescent whiteners, are colorless transparent compounds, which do not dye because they do not absorb light in the visible region, but only in the ultraviolet region (for example, wavelengths ranging from 200 to 400 nanometers), and convert the absorbed energy into fluorescent light of a longer wavelength emitted in the visible region of the spectrum; the color impression is then generated solely by purely fluorescent light that is predominantly blue (wavelengths ranging from 400 to 500 nanometers).

In another aspect of the present disclosure, the fluorescent dye used in the composition may be soluble in the medium of the composition. It should be pointed out that the fluorescent dye differs therein from a fluorescent pigment, which itself is insoluble in the medium of the composition.

In yet another aspect of the present disclosure, the fluorescent dye used in the context of the present disclosure, which may be optionally neutralized, can be soluble in the medium of the composition, for example to at least 0.001 g/l, further for example, to at least 0.5 g/l, in yet another example, to at least 1 g/l and, and in another example, to at least 5 g/l, with each of the preceding solubilities corresponding with a temperature of between 15 and 25° C.

In another aspect of the present disclosure, the composition does not comprise, as fluorescent dye, a 2-[2-(4-dialkylamino)phenylethenyl]-1-alkylpyridinium, wherein the alkyl radical of the pyridinium nucleus represents a methyl or ethyl radical and the alkyl radical of the benzene nucleus represents a methyl radical, and wherein the counterion is a halide.

In yet another aspect of the present disclosure, the composition does not comprise, as fluorescent dye, a compound chosen from azo, azomethine or methine monocationic heterocyclic fluorescent dyes.

In one embodiment, the fluorescent dye forming part of the composition according to the present disclosure does not comprise three fused rings of which one is a monocationic heterocycle comprising two nitrogen atoms. In another embodiment of the present disclosure, the composition does not comprise, as fluorescent dye, a compound comprising three fused aromatic nuclei, of which one comprises an oxygen atom.

For instance, the fluorescent dyes used according to the present disclosure may be dyes in the orange range.

In one embodiment, the fluorescent dyes of the present disclosure may lead to a reflectance maximum that is in the wavelength range from 500 to 650 nanometers, for example, in the wavelength range from 550 to 620 nanometers.

Some of the fluorescent dyes according to the present disclosure are compounds that are known per se.

As examples of fluorescent dyes that may be used according to the present disclosure, non-limiting mention may be made of the fluorescent dyes belonging to the following families: naphthalimides; cationic or non-cationic coumarins; xanthenodi-quinolizines (such as, sulphorhodamines); azaxanthenes; naphtholactams; azlactones; oxazines; thiazines; dioxazines; polycationic fluorescent dyes of azo, azomethine or methine type, alone or as mixtures, and further for example belonging to the following families: naphthalimides; cationic or non-cationic coumarins; azaxanthenes; naphtholactams; azlactones; oxazines; thiazines; dioxazines; polycationic fluorescent dyes of azo, azomethine or methine type, alone or as mixtures.

For example, non-limiting mention may be made of the following dyes:

Brilliant Yellow B6GL sold by the company Sandoz and having the following structure:

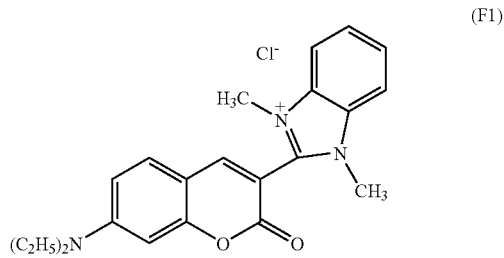

(F1)

Basic Yellow 2, or Auramine O, sold by the companies Prolabo, Aldrich or Carlo Erba and having the following structure:

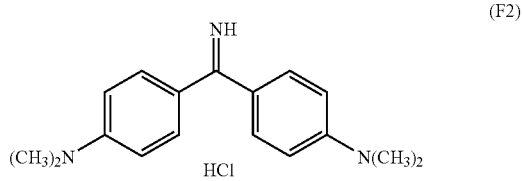

(F2)

4,4'-(imidocarbonyl)bis(N,N-dimethylaniline) monohydrochloride—CAS number 2465-27-2.

Non-limiting mention may also be made of compounds comprising the following formula:

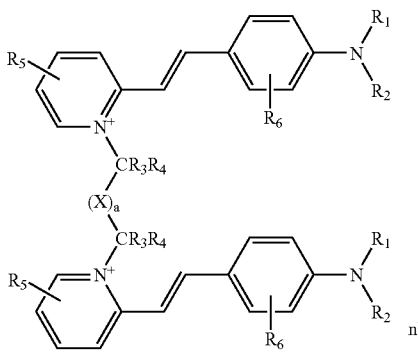

(F3)

wherein:

$R_1$ and $R_2$, which may be identical or different, may be chosen from:
- a hydrogen atom;
- linear or branched alkyl radicals comprising 1 to 10 carbon atoms for example, from 1 to 4 carbon atoms, optionally interrupted with at least one entity chosen from hetero atoms and groups comprising at least one hetero atom and optionally substituted with at least one entity chosen from hetero atoms and groups comprising at least one hetero atom and with at least one halogen atom; and
- aryl or arylalkyl radicals, the aryl group comprising 6 carbon atoms and the alkyl group comprising 1 to 4 carbon atoms; the aryl group optionally substituted with one or more linear or branched alkyl radicals comprising 1 to 4 carbon atoms optionally interrupted with at least one entity chosen from hetero atoms and groups comprising at least one hetero atom and/or optionally substituted with at least one entity chosen from hetero atoms and groups comprising at least one hetero atom, and with at least one halogen atom;

$R_1$ and $R_2$ may optionally be linked so as to form a heterocycle with the nitrogen atom and may comprise one or more other hetero atoms, the heterocycle optionally being substituted with at least one linear or branched alkyl radical, for example, comprising from 1 to 4 carbon atoms and optionally being interrupted and/or substituted with at least one hetero atom and/or group comprising at least one hetero atom and/or substituted with at least one halogen atom;

$R_1$ or $R_2$ may optionally be engaged in a heterocycle comprising the nitrogen atom and one of the carbon atoms of the phenyl group comprising said nitrogen atom;

$R_3$ and $R_4$, which may be identical or different, may be chosen from a hydrogen atom and alkyl radicals comprising 1 to 4 carbon atoms;

$R_5$, which may be identical or different, may be chosen from a hydrogen atom, a halogen atom, and linear or branched alkyl radicals comprising 1 to 4 carbon atoms, optionally interrupted with at least one hetero atom;

$R_6$, which may be identical or different, may be chosen from a hydrogen atom; a halogen atom; and linear or branched alkyl radicals comprising 1 to 4 carbon atoms, optionally interrupted with at least one entity chosen from hetero atoms and groups comprising at least one hetero atom and/or optionally substituted with at least one entity chosen from hetero atoms and groups comprising at least one hetero atom, and at least one halogen atom;

X may be chosen from:
- linear or branched alkyl radical comprising 1 to 14 carbon atoms or an alkenyl radical comprising 2 to 14 carbon atoms, optionally interrupted and/or substituted with at least one hetero atom and/or group comprising at least one hetero atom and/or substituted with at least one halogen atom;
- 5- or 6-membered heterocyclic radicals optionally substituted with at least one linear or branched alkyl radical comprising 1 to 14 carbon atoms, optionally substituted with at least one hetero atom; with at least one linear or branched aminoalkyl radical comprising 1 to 4 carbon atoms, optionally substituted with at least one hetero atom; or with at least one halogen atom;
- fused or non-fused aromatic or diaromatic radicals, optionally separated with at least one alkyl radical comprising 1 to 4 carbon atoms, the aryl radical optionally being substituted with at least one halogen atom or with at least one alkyl radical comprising 1 to 10 carbon atoms optionally substituted and optionally interrupted with at least one hetero atom and/or group comprising at least one hetero atom; and
- dicarbonyl radicals;

the group X optionally having one or more cationic charges;

a being equal to 0 or 1;

$Y^-$, which may be identical or different, may be chosen from organic and mineral anions; and n being an integer at least equal to 2 and at most equal to the number of cationic charges present in the fluorescent compound.

It should be recalled that the term "hetero atom" represents an oxygen or nitrogen atom.

Among the groups comprising such atoms, non-limiting mention may be made of hydroxyl, alkoxy, carbonyl, amino, ammonium, amido (—N—CO—) and carboxyl (—O—CO— or —CO—O—) groups.

As used herein the alkenyl groups may comprise one or more unsaturated carbon-carbon bonds (—C═C—), for example, only one carbon-carbon double bond.

In this general formula, the radicals $R_1$ and $R_2$, which may be identical or different, may be chosen from:
- a hydrogen atom;
- alkyl radicals comprising 1 to 10 carbon atoms, for example 1 to 6 carbon atoms and further for example, 1 to 4 carbon atoms, optionally interrupted with an oxygen atom or optionally substituted with at least one hydroxyl, amino or ammonium radical or a chlorine or fluorine atom; and
- benzyl or phenyl radicals optionally substituted with an alkyl or alkoxy radical comprising 1 to 4 carbon atoms, for example 1 or 2 carbon atoms;
- with the nitrogen atom, a heterocyclic radical of the pyrrolo, pyrrolidino, imidazolino, imidazolo, imidazolium, pyrazolino, piperazino, morpholino, morpholo, pyrazolo or triazolo type, optionally substituted with at least one linear or branched alkyl radical comprising 1 to 4 carbon atoms optionally interrupted and/or substituted with a nitrogen and/or oxygen atom and/or group comprising a nitrogen and/or oxygen atom.

As used herein, for the amino or ammonium radicals, the radicals borne by the nitrogen atom may be identical or different and may be chosen from a hydrogen atom, $C_1$-$C_{10}$, for example, $C_1$-$C_4$ alkyl radicals, and arylalkyl radicals wherein, the aryl radicals may comprise 6 carbon atoms and the alkyl radical comprises 1 to 10 carbon atoms, for example, 1 to 4 carbon atoms.

According to one embodiment of the present disclosure, the radicals $R_1$ and $R_2$, which may be identical or different, may be chosen from a hydrogen atom; linear or branched $C_1$-$C_6$ alkyl radicals; $C_2$-$C_6$ alkyl radicals substituted with a hydroxyl radical; $C_2$-$C_6$ alkyl radicals comprising an amino or ammonium group; $C_2$-$C_6$ chloroalkyl radicals; $C_2$-$C_6$ alkyl radicals interrupted with an oxygen atom or a group comprising an oxygen atom (for example ester); aromatic radicals, such as phenyl, benzyl and 4-methylphenyl; heterocyclic radicals such as pyrrolo, pyrrolidino, imidazolo, imidazolino, imidazolium, piperazino, morpholo, morpholino, pyrazolo, and triazolo radicals, optionally substituted with at least one $C_1$-$C_6$ alkyl or aromatic radicals.

In another embodiment of the present disclosure, the radicals $R_1$ and $R_2$, which may be identical or different, may be chosen from a hydrogen atom, linear and branched $C_1$-$C_6$ alkyl radicals, such as methyl, ethyl, n-butyl or n-propyl radicals; 2-hydroxyethyl; alkyltrimethylammonium and alkyltriethylammonium radicals, the alkyl radical being a linear $C_2$-$C_6$ alkyl radical; (di)alkylmethylamino and (di)alkylethylamino radicals, the alkyl radical being a linear $C_1$-$C_6$ alkyl radical; —$CH_2CH_2Cl$; —$(CH_2)_n$—$OCH_3$ and —$(CH_2)_n$—$OCH_2CH_3$ with n being an integer ranging from 2 to 6; —$CH_2CH_2$—$OCOCH_3$; and —$CH_2CH_2COOCH_3$.

In another aspect of the present disclosure, the radicals $R_1$ and $R_2$, which may be identical or different, are chosen from methyl radicals and ethyl radicals.

In yet another aspect of the present disclosure, the radicals $R_1$ and $R_2$, which may be identical or different, may also be chosen from heterocyclic radicals of the pyrrolidino, 3-aminopyrrolidino, 3-(dimethyl)aminopyrrolidino, 3-(trimethyl)aminopyrrolidino, 2,5-dimethylpyrrolo, 1H-imidazolo, 4-methylpiperazino, 4-benzylpiperazino, morpholo, 3,5-(tert-butyl)-1H-pyrazolo, 1H-pyrazolo, and 1H-1,2,4-triazolo type.

In another aspect of the present disclosure, the radicals $R_1$ and $R_2$, which may be identical or different, may be linked so as to form a heterocycle of formula (I) and (II) below:

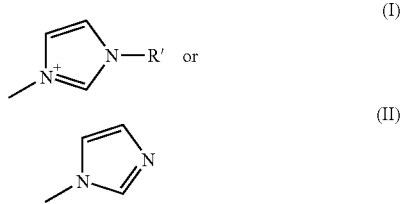

wherein R' is chosen from a hydrogen atom, $C_1$-$C_3$ alkyl radicals, —$CH_2CH_2OH$, and —$CH_2CH_2OCH_3$.

In one embodiment of the present disclosure, $R_5$, which may be identical or different, is chosen from a hydrogen atom, fluorine and chlorine atoms, and linear and branched alkyl radicals comprising 1 to 4 carbon atoms optionally interrupted with an oxygen or nitrogen atom.

For example, the substituent $R_5$, if it is other than hydrogen, may be in position(s) 3 and/or 5 relative to the carbon of the ring bearing the nitrogen substituted with the radicals $R_1$ and $R_2$, for instance in position 3 relative to that carbon.

In another example, the radicals $R_5$, which may be identical or different, may be chosen from a hydrogen atom; linear and branched $C_1$-$C_4$ alkyl radicals; —O—$R_{51}$ wherein $R_{51}$ is chosen from linear $C_1$-$C_4$ alkyl radicals; —$R_{52}$—O—$CH_3$ wherein $R_{52}$ is chosen from linear $C_2$-$C_3$ alkyl radicals; —$R_{53}$—$N(R_{54})_2$ wherein $R_{53}$ is chosen from linear $C_2$-$C_3$ alkyl radicals and $R_{54}$, which may be identical or different, is chosen from a hydrogen atom and methyl radicals.

In yet another example, $R_5$, which may be identical or different, is chosen from a hydrogen atom, a methyl, and a methoxy group. In one embodiment, $R_5$ represents a hydrogen atom.

According to one aspect of the present disclosure, the radicals $R_6$, which may be identical or different, is chosen from a hydrogen atom; linear and branched $C_1$-$C_4$ alkyl radicals; —X wherein X is chosen from chlorine, bromine and fluorine atoms; —$R_{61}$—O—$R_{62}$ wherein $R_{61}$ may be chosen from linear $C_2$-$C_3$ alkyl radicals and $R_{62}$ is chosen from methyl radicals; —$R_{63}$—$N(R_{64})_2$ wherein $R_{63}$ is chosen from linear $C_2$-$C_3$ alkyl radicals and $R_{64}$, which may be identical or different, is chosen from a hydrogen atom and methyl radicals; —$N(R_{65})_2$ wherein $R_{65}$, which may be identical or different, is chosen from a hydrogen atom and linear $C_2$-$C_3$ alkyl radicals; —$NHCOR_{66}$ wherein $R_{66}$ is chosen from $C_1$-$C_2$ alkyl radicals, $C_1$-$C_2$ chloroalkyl radicals, radicals —$R_{67}$—$NH_2$, and —$R_{67}$—$NH(CH_3)$, and —$R_{67}$—$N(CH_3)_2$, and —$R_{67}$—$N^+(CH_3)_3$, and —$R_{67}$—$N^+(CH_2CH_3)_3$, wherein $R_{67}$ is chosen from $C_1$-$C_2$ alkyl radicals.

In another aspect of the present disclosure, the substituent $R_6$, if it is other than hydrogen, may be in position(s) 2 and/or 4 relative to the nitrogen atom of the pyridinium ring, for example, in position 4 relative to that nitrogen atom.

For instance, these radicals $R_6$, which may be identical or different, may be chosen from a hydrogen atom and methyl and ethyl radicals. In one embodiment, $R_6$ represents a hydrogen atom.

In another aspect of the present disclosure, the radicals $R_3$ and $R_4$, which may be identical or different, may be chosen from a hydrogen atom and alkyl radicals comprising 1 to 4 carbon atoms, for example a methyl radical. In one embodiment, $R_3$ and $R_4$ each represent a hydrogen atom.

As mentioned above, X may be chosen from:
  linear or branched alkyl radicals comprising 1 to 14 carbon atoms and alkenyl radicals comprising 2 to 14 carbon atoms, optionally interrupted with at least one entity chosen from hetero atoms, with at least one group comprising at least one hetero atom and/or with at least one halogen atom, and/or optionally substituted with at least one entity chosen from hetero atoms, with at least one group comprising at least one hetero atom and/or with at least one halogen atom;
  5- or 6-membered heterocyclic radicals optionally substituted with at least one linear or branched alkyl radical comprising 1 to 14 carbon atoms, with at least one linear or branched aminoalkyl radical comprising 1 to 4 carbon atoms, optionally substituted with at least one hetero atom; or with at least one halogen atom;
  fused or non-fused aromatic and diaromatic radicals, optionally separated with at least one alkyl radical comprising 1 to 4 carbon atoms, the aryl radical(s) optionally being substituted with at least one halogen atom or with at least one alkyl radical comprising 1 to 10 carbon atoms optionally substituted and/or interrupted with at least one hetero atom and/or group comprising at least one hetero atom; and
  dicarbonyl radicals.

In one example, the group X may bear one or more cationic charges.

In yet another aspect of the present disclosure, X may be chosen from linear and branched alkyl radicals comprising 1 to 14 carbon atoms and alkenyl radicals comprising 2 to 14 carbon atoms, and may be substituted and/or interrupted with one or more oxygen and/or nitrogen atoms, and/or with one or more groups comprising at least one hetero atom, and/or with one or more fluorine and chlorine atoms.

Among the groups of this type, non-limiting mention may be made of hydroxyl, alkoxy (such as those with a radical R of the $C_1$-$C_4$ alkyl type), amino, ammonium, amido, carbonyl, and carboxyl groups (—COO— or —O—CO—), for example those with a radical of alkyloxy type.

In one aspect of the present invention the nitrogen atom, if it is present, may be in a quaternized or non-quaternized form. In this case, the other radical or the other two radicals borne by the quaternized or non-quaternized nitrogen atom may be identical or different and may be a hydrogen atom or a $C_1$-$C_4$ alkyl radical, such as a methyl group.

According to another apsect of the present disclosure, the group X may be chosen from 5- or 6-membered heterocyclic radicals of the imidazolo, pyrazolo, triazino, and pyridino type, optionally substituted with one or more linear or branched alkyl radicals comprising from 1 to 14 carbon atoms, for example, 1 to 10 carbon atoms, and further for example from 1 to 4 carbon atoms; with at least one linear or branched aminoalkyl radical comprising 1 to 10 carbon atoms, for example from 1 to 4 carbon atoms, optionally substituted with a group comprising at least one hetero atom (preferably a hydroxyl radical), or with a halogen atom. In one embodiment, the amino group may be linked to the heterocycle.

In accordance with another aspect of the present disclosure, the group X may be chosen from aromatic radicals (such as those comprising 6 carbon atoms), and fused and non-fused diaromatic radicals (such as those comprising from 10 to 12 carbon atoms), optionally separated with at least one alkyl radical comprising 1 to 4 carbon atoms, the aryl radical(s) optionally being substituted with at least one halogen atom and/or with at least one alkyl radical comprising 1 to 10 carbon atoms, for example 1 to 4 carbon atoms, optionally interrupted with at least one oxygen and/or nitrogen atom and/or a group comprising at least one hetero atom (chosen from, for instance, carbonyl, carboxyl, amido, amino and ammonium radicals).

In one example, the aromatic radical, such as a phenyl radical, may be linked to the groups $CR_3R_4$ via bonds in positions 1,2; 1,3; or 1,4 and further for example, in positions 1,3 and 1,4. If the phenyl radical linked via bonds in positions 1,4 bears one or two substituents, this or these substituent(s) may be located, for instance, in position 1,4 relative to one of the groups $CR_3R_4$. If the phenyl radical linked via bonds in positions 1,3 bears one or two substituents, this or these substituents may be located, for instance, in position 1 and/or 3 relative to one of the groups $CR_3R_4$.

In one aspect of the present disclosure, where the radical is diaromatic, it may be, for example, non-fused and comprise two phenyl radicals optionally separated with a single bond (i.e. a carbon of each of the two rings) or with an alkyl radical, such as $CH_2$ or $C(CH_3)_2$. In another example, the aromatic radicals do not bear a substituent. In a yet another aspect, said diaromatic radical may be linked to the groups $CR_3R_4$ via bonds in positions 4,4'.

As examples of groups X that are suitable, non-limiting mention may be made of linear or branched alkyl radicals comprising 1 to 13 carbon atoms, such as methylene, ethylene, propylene, isopropylene, n-butylene, pentylene and hexylene; 2-hydroxypropylene and 2-hydroxy-n-butylene; $C_1$-$C_{13}$ alkylene radicals substituted or interrupted with one or more nitrogen and/or oxygen atoms, and/or groups comprising at least one hetero atom (hydroxyl, amino, ammonium, carbonyl or carboxyl, for example), such as —$CH_2CH_2OCH_2CH_2$—, 1,6-dideoxy-d-mannitol, —$CH_2N^+(CH_3)_2CH_2$—, —$CH_2CH_2N^+(CH_3)_2$—$(CH_2)_6N^+$ $(CH_3)_2$—$CH_2CH_2$—, CO—CO—, 3,3-dimethylpentylene, 2-acetoxyethylene, butylene-1,2,3,4-tetraol; —CH=CH—; aromatic or diaromatic radicals substituted with one or more alkyl radicals, with one or more groups comprising at least one hetero atom and/or with one or more halogen atoms, such as 1,4-phenylene, 1,3-phenylene, 1,2-phenylene, 2,6-fluorobenzene, 4,4'-biphenylene, 1,3-(5-methylbenzene), 1,2-bis(2-methoxy)benzene, bis(4-phenyl)methane, methyl 3,4-benzoate and 1,4-bis(amidomethyl)phenyl; radicals of heterocyclic type such as pyridine, and derivatives such as 2,6-bispyridine, imidazole, imidazolium, or triazine.

According to another embodiment of the present disclosure, X may be chosen from linear and branched $C_1$-$C_{13}$ alkyl radicals; —$CH_2CH(OH)CH_2$—; —$CH_2CH(Cl)$ $CH_2$—; —$CH_2CH_2$—$OCOCH_2$—; —$CH_2CH_2COOCH_2$—; —Ra—O—Rb— with Ra chosen from linear $C_2$-$C_6$ alkyl radicals and Rb representing linear $C_1$-$C_2$ alkyl radicals; —Rc—N(Rd)—Re— with Rc chosen from $C_2$-$C_9$ alkyl radicals, Rd chosen from a hydrogen atom and $C_1$-$C_2$ alkyl radicals and Re chosen from $C_1$-$C_6$ alkyl radicals; —Rf—$N^+(Rg)_2$—Rh— with Rf chosen from linear $C_2$-$C_9$ alkyl radicals, Rg, which may be identical, chosen from $C_1$-$C_2$ alkyl radicals, and Rh chosen from linear $C_1$-$C_6$ alkyl radicals; and —CO—CO—.

In another aspect of the present disclosure X may be chosen from imidazole radicals, optionally substituted with at least one alkyl radical comprising 1 to 14 carbon atoms, for example 1 to 10 carbon atoms and in another example 1 to 4 carbon atoms, and in yet another example the divalent radicals having the following formula:

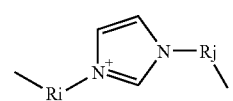

(III)

wherein Ri and Rj, which may be identical or different, may be chosen from linear $C_1$-$C_6$ alkyl radicals.

In another aspect of the present disclosure, X may similarly be chosen from the divalent triazine-based radicals below:

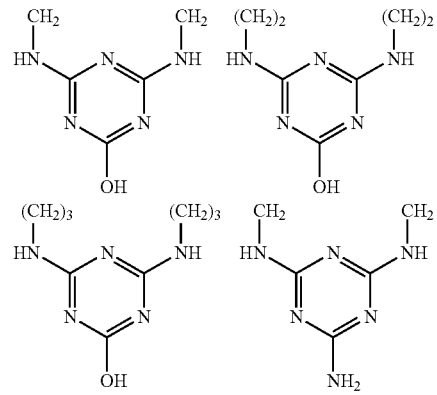

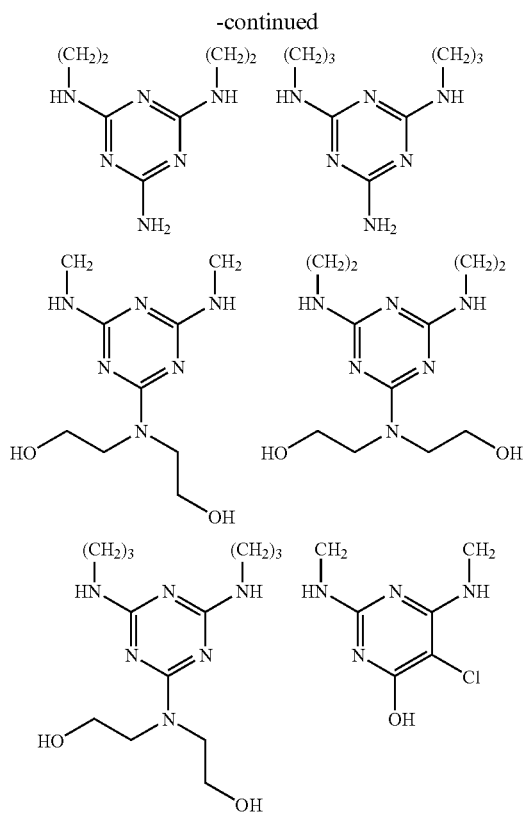

According to yet another aspect of the present invention, X may represent the divalent aromatic radicals below:

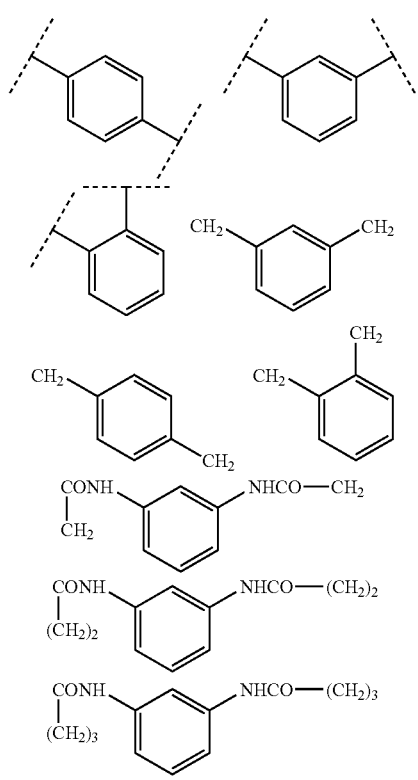

In another aspect of the present disclosure, Y⁻ may be chosen from organic or mineral anions. If there are several anions Y⁻, these anions may be identical or different.

Among the anions of mineral origin non-limiting mention may be made of anions derived from halogen atoms, such as chlorides, iodides, sulphates, bisulphates, nitrates, phosphates, hydrogen phosphates, dihydrogen phosphates, carbonates, and bicarbonates.

Among the anions of organic origin non-limiting mention may be made of anions derived from the salts of saturated or unsaturated, aromatic or non-aromatic monocarboxylic or polycarboxylic, sulphonic or sulphuric acids, optionally substituted with at least one hydroxyl or amino radical, or halogen atoms. Non-limiting examples that are suitable for use include acetates, hydroxyacetates, aminoacetates, (tri)chloroacetates, benzoxyacetates, propionates and derivatives comprising a chlorine atom, fumarates, oxalates, acrylates, malonates, succinates, lactates, tartrates, glycolates, citrates, benzoates and derivatives comprising a methyl radicals, amino radicals, alkyl sulphates, tosylates, benzenesulphonates, and toluenesulphonates.

In yet another aspect of the present disclosure, the at least one anion Y, which may be identical or different, may be chosen from chloride, sulphate, methosulphate, and ethosulphate.

In another aspect of the present disclosure, the integer n is at least equal to 2 and at most equal to the number of cationic charges present in the fluorescent compound.

In yet another aspect of the present disclosure, the fluorescent compounds that have just been described in detail may be symmetrical compounds.

In one embodiment, these compounds may be synthesized by reacting, in a first step, α-picoline with a reagent comprising two leaving groups that may be chosen from halogen atoms, such as bromine, and chlorine, or groups of the tolylsulphonyl type and groups of the methanesulphonyl type.

In a further embodiment, this first step may take place in the presence of a solvent, although this is not obligatory, for instance dimethylformamide.

In one example, the number of moles of α-picoline may be in the region of 2 per mole of reagent comprising the leaving groups.

In another example, the reaction may be performed at the reflux temperature of the reagent and/or of the solvent, if a solvent is present.

The product derived from this first step may then be placed in contact with a corresponding aldehyde having the following formula:

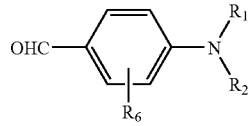

wherein $R_1$, $R_2$ and $R_6$ have the same meanings as indicated above.

In this case also, the reaction may be performed in the presence of a suitable solvent, which, for example, may be at reflux.

In another aspect of the present disclosure the radicals $R_1$ and $R_2$ of the aldehyde may have the meaning indicated in the general formula detailed previously.

In one embodiment, it is also possible to use an aldehyde for which said radicals represent hydrogen atoms and to perform, in accordance with standard methods, the substitution of these hydrogen atoms with suitable radicals as described in the general formula once the second step is complete.

Reference may be made especially to syntheses as described in U.S. Pat. No. 4,256,458.

The at least one fluorescent dye present in the composition according to the present disclosure may be present in an amount from 0.01% to 20% by weight, for example, from 0.05% to 10% by weight and further, for example, from 0.1% to 5% by weight, relative to the total weight of the composition.

The cosmetically acceptable medium may comprise water or a mixture of water and one or more common organic solvents.

Among the solvents that are suitable for use, non-limiting mention may be made of alcohols such as ethyl alcohol, isopropyl alcohol, benzyl alcohol and phenylethyl alcohol, or glycols or glycol ethers, for instance ethylene glycol monomethyl ether, monoethyl ether or monobutyl ether, propylene glycol and ethers thereof, for instance propylene glycol monomethyl ether, butylene glycol, dipropylene glycol and diethylene glycol alkyl ethers, for instance diethylene glycol monoethyl ether or monobutyl ether, or alternatively polyols, for instance glycerol. Polyethylene glycols and polypropylene glycols, and mixtures of all these compounds, may also be used as a solvent.

For example, the common solvents described herein may be present in an amount ranging from 1% to 40% by weight, and further, for example, from 5% to 30% by weight relative to the total weight of the composition.

Further for example, the pH of the composition in accordance with the present disclosure may be between 3 and 12, for example, between 5 and 11.

It may be adjusted to the desired value by means of acidifying or basifying agents commonly used in the field.

Examples of acidifying agents that non-limiting mention may be made of include mineral or organic acids, for instance hydrochloric acid, orthophosphoric acid, sulphuric acid, carboxylic acids, for instance acetic acid, tartaric acid, citric acid and lactic acid, and sulphonic acids.

Examples of basifying agents that non-limiting mention may be made of include aqueous ammonia, alkaline carbonates, alkanolamines such as monoethanolamine, diethanolamine and triethanolamine and derivatives thereof, sodium hydroxide, potassium hydroxide and the compounds of formula (A) below:

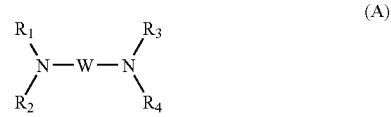

wherein W is a propylene residue optionally substituted with a hydroxyl group or a $C_1$-$C_6$ alkyl radical; $R_1$, $R_2$, $R_3$ and $R_4$, which may be identical or different, are chosen from a hydrogen atom and $C_1$-$C_6$ alkyl or $C_1$-$C_6$ hydroxyalkyl radicals.

According to one embodiment of the present disclosure, the composition may comprise, in addition to the at least one fluorescent dye, one or more additional non-fluorescent direct dyes of nonionic, cationic or anionic nature, which may be chosen, for example, from nitrobenzene dyes.

For example, the following red or orange nitrobenzene direct dyes may be suitable for use:
1-hydroxy-3-nitro-4-N-(γ-hydroxypropyl)aminobenzene,
N-(β-hydroxyethyl)amino-3-nitro-4-aminobenzene,
1-amino-3-methyl-4-N-(β-hydroxyethyl)amino-6-nitrobenzene,
1-hydroxy-3-nitro-4-N-(β-hydroxyethyl)aminobenzene,
1,4-diamino-2-nitrobenzene,
1-amino-2-nitro-4-methylaminobenzene,
N-(β-hydroxyethyl)-2-nitro-para-phenylenediamine,
1-amino-2-nitro-4-(β-hydroxyethyl)amino-5-chlorobenzene,
2-nitro-4-aminodiphenylamine,
1-amino-3-nitro-6-hydroxybenzene,
1-(β-aminoethyl)amino-2-nitro-4-(β-hydroxyethyloxy)benzene,
1-(β,γ-dihydroxypropyl)oxy-3-nitro-4-(β-hydroxyethyl) aminobenzene,
1-hydroxy-3-nitro-4-aminobenzene,
1-hydroxy-2-amino-4,6-dinitrobenzene,
1-methoxy-3-nitro-4-(β-hydroxyethyl)aminobenzene,
2-nitro-4'-hydroxydiphenylamine, and
1-amino-2-nitro-4-hydroxy-5-methylbenzene.

In another aspect, the composition in accordance with the present disclosure may also comprise, in addition to or in replacement for these nitrobenzene dyes, one or more additional direct dyes chosen from yellow, green-yellow, blue and violet nitrobenzene dyes, azo dyes, anthraquinone dyes, naphthoquinone dyes, benzoquinone dyes, indigoid dyes, and triarylmethane-based dyes.

For example, these additional direct dyes may be basic dyes, among which non-limiting mention may be made of the dyes known in the Color Index, 3rd edition, under the names "Basic Brown 16", "Basic Brown 17", "Basic Yellow 57", "Basic Red 76", "Basic Violet 10", "Basic Blue 26" and "Basic Blue 99"; or acidic direct dyes, among which non-limiting mention may be made of the dyes known in the Colorr Index, 3rd edition, under the names "Acid Orange 7", "Acid Orange 24", "Acid Yellow 36", Acid Red 33", "Acid Red 184", "Acid Black 2", "Acid Violet 43" and "Acid Blue 62", or alternatively cationic direct dyes such as those described in patent applications WO 95/01772, WO 95/15144 and EP-A-0714954, the contents of which relating to such cationic direct dyes are incorporated herein by reference.

Among the additional yellow and green-yellow nitrobenzene direct dyes, non-limiting mention may be made of compounds chosen from:

1-β-hydroxyethyloxy-3-methylamino-4-nitrobenzene,
1-methylamino-2-nitro-5-(β,γ-dihydroxypropyl)oxybenzene,
1-(β-hydroxyethyl)amino-2-methoxy-4-nitrobenzene,
1-(β-aminoethyl)amino-2-nitro-5-methoxybenzene,
1,3-di(β-hydroxyethyl)amino-4-nitro-6-chlorobenzene,
1-amino-2-nitro-6-methylbenzene,
1-(β-hydroxyethyl)amino-2-hydroxy-4-nitrobenzene,
N-(β-hydroxyethyl)-2-nitro-4-trifluoromethylaniline,
4-(β-hydroxyethyl)amino-3-nitrobenzenesulphonic acid,
4-ethylamino-3-nitrobenzoic acid,
4-(β-hydroxyethyl)amino-3-nitrochlorobenzene,
4-(β-hydroxyethyl)amino-3-nitromethylbenzene,
4-(β,γ-dihydroxypropyl)amino-3-nitrotrifluoromethylbenzene,
1-(β-ureidoethyl)amino-4-nitrobenzene,
1,3-diamino-4-nitrobenzene,
1-hydroxy-2-amino-5-nitrobenzene,
1-amino-2-[tris(hydroxymethyl)methyl]amino-5-nitrobenzene,
1-(β-hydroxyethyl)amino-2-nitrobenzene, and
4-(β-hydroxyethyl)amino-3-nitrobenzamide.

Among the additional blue or violet nitrobenzene direct dyes that may be used, non-limiting mention may be made of compounds chosen from:

1-(β-hydroxyethyl)amino-4-N,N-bis(β-hydroxyethyl) amino-2-nitrobenzene,
1-(γ-hydroxypropyl)amino-4,N,N-bis(β-hydroxyethyl) amino-2-nitrobenzene,
1-(β-hydroxyethyl)amino-4-(N-methyl-N-β-hydroxyethyl) amino-2-nitrobenzene,
1-(β-hydroxyethyl)amino-4-(N-ethyl-N-β-hydroxyethyl) amino-2-nitrobenzene,
1-(β,γ-dihydroxypropyl)amino-4-(N-ethyl-N-β-hydroxyethyl)amino-2-nitrobenzene, and
2-nitroparaphenylenediamines having the following formula:

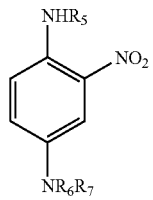

wherein:
$R_6$ is chosen from $C_1$-$C_4$ alkyl radicals and β-hydroxyethyl, β-hydroxypropyl and γ-hydroxypropyl radicals;
$R_5$ and $R_7$, which may be identical or different, are chosen from β-hydroxyethyl, β-hydroxypropyl, γ-hydroxypropyl and β,γ-dihydroxypropyl radicals, at least one of the radicals $R_6$, $R_7$ or $R_5$ is chosen from γ-hydroxypropyl radicals and $R_6$ and $R_7$ not simultaneously being able to denote a β-hydroxyethyl radical when $R_6$ is a γ-hydroxypropyl radical, such as those described in patent application FR 2,692,572.

When present, the additional at least one direct dye may be present in an amount ranging from 0.0005% to 12% by weight, relative to the total weight of the composition, for example from 0.005% to 6% by weight, relative to this weight.

In another aspect of the present disclosure, when it is intended for oxidation dyeing, the composition in accordance with the present disclosure comprises, in addition to the at least one fluorescent dye, at least one oxidation base chosen from the oxidation bases conventionally used for oxidation dyeing and among which non-limiting mention may be made of para-phenylenediamines, bis(phenyl)alkylenediamines, para-aminophenols, ortho-aminophenols and heterocyclic bases, and the addition salts thereof with an acid or with an alkaline agent.

Among the para-phenylenediamines that may be used, non-limiting mention may be made of para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxy-ethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, and 4'-aminophenyl-1-(3-hydroxy) pyrrolidine, and the addition salts thereof with an acid or with an alkaline agent.

For example, the para-phenylenediamines may be chosen from para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethylpara-phenylenediamine, 2,3-dimethyl-para-phenylenediamine, N,N-bis(β-hydroxyethyl)-para-phenylenediamine, 2-chloro-para-phenylenediamine, and 2-β-acetylaminoethyloxy-para-phenylenediamine, and the addition salts thereof with an acid or with an alkaline agent.

Among the bis(phenyl)alkylenediamines that may be used, non-limiting mention may be made of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, and 1,8-bis(2,5-diaminophenoxy)-3,5-dioxaoctane, and the addition salts thereof with an acid or with an alkaline agent.

Among the para-aminophenols that may be used, non-limiting mention may be made of para-aminophenol, 4-amino-3-methyl phenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, and 4-amino-2-fluorophenol, and the addition salts thereof with an acid or with an alkaline agent.

Among the ortho-aminophenols that may be used, non-limiting mention may be made of 2-aminophenol, 2-amino-5-methylphenol, 2-amino-6-methylphenol, and 5-acetamido-2-aminophenol, and the addition salts thereof with an acid or with an alkaline agent.

Among the heterocyclic bases that may be used, non-limiting mention may be made of pyridine derivatives, pyrimidine derivatives, and pyrazole derivatives, and the addition salts thereof with an acid or with an alkaline agent.

When they are used, the oxidation base(s) may be present in an amount ranging from 0.0005% to 12% by weight, relative to the total weight of the composition, for example from 0.005% to 6% by weight, relative to this weight.

In one aspect of the present disclosure, when it is intended for oxidation dyeing, the composition in accordance with the present disclosure may also comprise, in addition to the fluorescent dyes and the oxidation bases, at least one coupler so as to modify or to enrich with glints the shades obtained using the fluorescent dyes and the oxidation base(s).

For example, the couplers that may be used in the composition in accordance with the present disclosure may be chosen from the couplers conventionally used in oxidation dyeing, and among which non-limiting mention may be made of meta-phenylenediamines, meta-aminophenols, meta-diphenols, and heterocyclic couplers, and the addition salts thereof with an acid or with an alkaline agent.

Further for example, these couplers may be chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole, and 6-methylpyrazolo[1,5-a]benzimidazole, and the addition salts thereof with an acid or with an alkaline agent.

When they are present, the coupler(s) may be present in an amount ranging from 0.0001% to 10% by weight, relative to the total weight of the composition, for example from 0.005% to 5% by weight, relative to this weight.

In one aspect of the present disclosure, the addition salts with an acid that may be used in the context of the compositions of the present disclosure (oxidation bases and couplers) may be chosen from the hydrochlorides, hydrobromides, sulphates, citrates, succinates, tartrates, tosylates, benzenesulphonates, lactates, and acetates.

In another aspect of the present disclosure, the addition salts with an alkaline agent that may be used in the context of the compositions of the present disclosure (oxidation bases and couplers) may be chosen from the addition salts with alkali metals or alkaline-earth metals, with ammonia, and with organic amines, such as alkanolamines and the compounds of formula (A).

In yet another aspect, the composition in accordance with the present disclosure may further comprise at least one of various adjuvants conventionally used in compositions, such as anionic, cationic, nonionic, amphoteric and zwitterionic surfactants, anionic, cationic, nonionic, amphoteric and zwitterionic polymers other than those of the present disclosure, mineral thickeners, antioxidants, penetrating agents, sequestering agents, fragrances, buffers, dispersants, conditioners, for instance cations, volatile and non-volatile, modified and unmodified silicones, film-forming agents, ceramides, preserving agents, stabilizers, and opacifiers.

According to one embodiment, it is also possible to add organic associative thickening polymers to the composition in accordance with the present disclosure.

When one or more surfactants are present, such as nonionic, anionic or amphoteric type surfactants, they may be present in an amount ranging from 0.01% to 30% by weight relative to the weight of the composition.

Needless to say, a person skilled in the art will take care to select this or these optional additional compound(s) such that the advantageous properties intrinsically associated with the composition disclosed herein are not, or are not substantially, adversely affected by the envisaged addition(s).

The composition according to the present disclosure may be in various forms, such as in the forms chosen from liquids, shampoos, creams, gels, and in any other suitable form.

In one embodiment, the composition is in the form of a lightening dye shampoo comprising, in a cosmetically acceptable aqueous medium, at least one fluorescent dye that is soluble in the medium and at least one non-associative thickening polymer as disclosed herein.

In another embodiment according to the present disclosure, when one or more oxidation bases are used, optionally in the presence of one or more couplers, or when the at least one fluorescent dye is used in the context of a lightening direct dyeing, then the composition may further comprise at least one oxidizing agent.

For example, the oxidizing agent may be chosen from hydrogen peroxide, urea peroxide, alkali metal bromates, persalts such as perborates and persulphates, and enzymes such as peroxidases and two-electron and four-electron oxidoreductases. In one embodiment, the oxidizing agent is chosen from hydrogen peroxide and enzymes.

Another aspect of the present disclosure is also a method for dyeing human keratin materials with a lightening effect, with a composition comprising, in a cosmetically acceptable medium, at least one fluorescent dye that is soluble in said medium, and at least one non-associative thickening polymer chosen from the group comprising:
- (i) crosslinked acrylic acid homopolymers;
- (ii) crosslinked 2-acrylamido-2-methylpropanesulphonic acid homopolymers and the partially or totally neutralized acrylamide crosslinked copolymers thereof;
- (iii) ammonium acrylate homopolymers and copolymers of ammonium acrylate and of acrylamide;
- (iv) dimethylaminoethyl methacrylate homopolymers quaternized with methyl chloride, and copolymers of dimethylaminoethyl methacrylate quaternized with methyl chloride and of acrylamide;
- (v) nonionic guar gums;
- (vi) biopolysaccharide gums of microbial origin, such as scleroglucan gum and xanthan gum;
- (vii) gums derived from plant exudates, such as gum arabic, ghatti gum, karaya gum and gum tragacanth;
- (viii) hydroxypropyl or carboxymethyl celluloses;
- (ix) pectins; and
- (x) alginates.

In the context of this use, the at least one fluorescent compound, for example, may be chosen from fluorescent compounds belonging to the following families: naphthalimides; cationic and non-cationic coumarins; xanthenodiquinolizines (especially such as sulphorhodamines); azaxanthenes; naphtholactams; azlactones; oxazines; thiazines; dioxazines; and monocationic and polycationic fluorescent dyes of azo, azomethine and methine type, alone and as mixtures.

Further for example, other compounds that non-limiting mention may be made of include the compounds of formulae F1, F2 and F3 already detailed previously.

In yet another example, it is also possible to use the compounds of structure (F4) below:

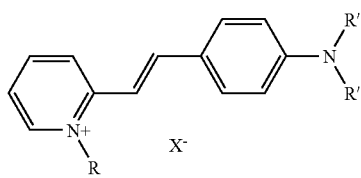

wherein formula R is chosen from methyl and ethyl radicals; R' is chosen from methyl radicals, and X$^-$ is chosen from anions such as chloride, iodide, sulphate, methosulphate, acetate, and perchlorate. An example of a compound of this type that may be mentioned is the Photosensitizing Dye NK-557 sold by the company Ubichem, wherein R is chosen from ethyl radicals, R' is chosen from methyl radicals and X$^-$ is chosen from an iodide.

Everything that has been described previously regarding the natures and contents of the various additives present in the composition remains valid and will not be repeated in this section.

According to the present disclosure, the term "human keratin materials" means the skin, the hair, the nails, the eyelashes and the eyebrows, for example, dark skin and artificially colored or pigmented hair.

For the purposes of the present disclosure, the term "dark skin" means a skin whose lightness L* measured in the CIEL L*a*b* system is less than or equal to 45, for example less than or equal to 40, given that L*=0 is equivalent to black and L*=100 is equivalent to white. For instance, skin types corresponding to this lightness include African skin, African-American skin, hispano-American skin, Indian skin and North African skin.

For the purposes of the present disclosure, the expression "artificially dyed or pigmented hair" means hair whose tone height is less than or equal to 6 (dark blond), for example less than or equal to 4 (chestnut-brown).

The lightening of the hair is evaluated by the "tone height," which characterizes the degree or level of lightening. The notion of "tone" is based on the classification of the natural shades, one tone separating each shade from the shade immediately following or preceding it. This definition and the classification of the natural shades are well known to hairstyling professionals and are published in the book "Sciences des traitements capillaires [Hair treatment sciences]" by Charles Zviak, 1988, published by Masson, pp. 215 and 278.

The tone heights range from 1 (black) to 10 (light blond), one unit corresponding to one tone; the higher the figure, the lighter the shade.

Another aspect of the present disclosure is a process for dyeing human keratin fibers with a lightening effect, comprising the following steps:
- a) applying to keratin fibers a composition according to the present disclosure, for a time that is sufficient to develop the desired coloration and lightening,
- b) optionally rinsing said fibers,
- c) optionally washing said fibers with shampoo and rinsing,
- d) drying or leaving to dry said fibers.

Yet another aspect of the present disclosure is a process for coloring dark skin with a lightening effect, wherein the composition that has just been described is applied to the skin and the skin is then dried or is left to dry.

Everything that has been described previously regarding the various constituent components of the composition remains valid, and reference may be made thereto.

For example, the processes according to the present disclosure may be suitable for treating human keratin fibers, such as artificially colored or pigmented hair, and dark skin.

Further for example, the fibers that may be treated with the process of the present disclosure may have a tone height of less than or equal to 6 (dark blond) for instance, less than or equal to 4 (chestnut-brown).

In yet another example, a dark skin capable of being treated in accordance with the present disclosure has a lightness L*, measured in the CIEL L*a*b* system, of less than or equal to 45, for instance less than or equal to 40.

In one embodiment of the present disclosure, the process of dyeing fibers with a lightening effect may be performed with a composition that does not comprise any oxidation dyes or coupler and in the absence of oxidizing agent.

In another embodiment of the present disclosure, the process of dyeing fibers with a lightening effect may be performed with a composition that does not comprise any oxidation dyes or coupler, but in the presence of oxidizing agent(s).

In another embodiment, at least one composition as defined above may be applied to the fibers, and especially the hair, for a time that is sufficient to develop the desired coloration and lightening, after which the fibers are rinsed, optionally washed with shampoo, rinsed again and dried.

In yet another embodiment of the dyeing processes in accordance with the present disclosure, at least one composition as defined above is applied to the fibers, such as the hair, for a time that is sufficient to develop the desired coloration and lightening, without final rinsing.

In another embodiment of the present disclosure, the dyeing process further comprises the steps of: (a) separately storing, a composition according to the present disclosure optionally comprising, in addition to the fluorescent compound and the non-associative thickening polymer, oxidation base and/or a coupler, and a second composition comprising, in a cosmetically acceptable medium, at least one oxidizing agent, and (b) mixing the two compositions together at the time of use, after which this mixture is applied to the keratin fibers, such as the hair, for a time that is sufficient to develop the desired coloration, after which the fibers are rinsed, optionally washed with shampoo, rinsed again and dried.

For example, the time required to develop the coloration and to obtain the lightening effect on the fibers, such as the hair, may range between about 5 to 60 minutes, for instance from about 5 to 40 minutes.

In another example, the temperature required to develop the coloration and to obtain the lightening effect may range from room temperature (15 to 25° C.) to 80° C., for instance from 15 and 40° C.

Another embodiment of the present disclosure is a multicompartment device for dyeing keratin fibers, such as the hair, with a lightening effect, comprising at least one compartment comprising a composition according to the present disclosure, and at least one other compartment comprising a composition comprising at least one oxidizing agent. For example, this device may be equipped with a means for applying the desired mixture to the fibers, such as the devices described in Patent No. FR 2,586,913.

It should be noted that the composition according to the present disclosure, if it is used to treat keratin fibers, for example such as chestnut-brown hair, makes it possible to achieve the following results.

If the reflectance of the hair is measured when it is irradiated with visible light in the wavelength range from 400 to 700 nanometers, and if the curves of reflectance as a function of the wavelength are compared for hair treated with the composition disclosed herein and untreated hair, it was found that the reflectance curve corresponding to the treated hair, in a wavelength range from 500 to 700 nanometers, was higher than that corresponding to the untreated hair.

This means that, in the wavelength range from 500 to 700 nanometers, for example from 540 to 700 nanometers, there is at least one range wherein the reflectance curve corresponding to the treated hair is higher than the reflectance curve corresponding to the untreated hair. As used herein, the term "higher than" means a difference of at least 0.05%, for example at least 0.1% of reflectance.

However, it is pointed out that there may be, within the wavelength range from 500 to 700 nanometers, for example from 540 to 700 nanometers, at least one range wherein the reflectance curve corresponding to the treated fibers is either superimposable on or lower than the reflectance curve corresponding to the untreated fibers.

For example, the wavelength at which the difference is maximal between the reflectance curve for the treated hair and that for the untreated hair is in the wavelength range from 500 to 650 nanometers, such as in the wavelength range from 550 to 620 nanometers.

Further for example, the composition may be capable of lightening the hair and the skin in a shade which, measured in the CIEL L*a*b* system, has a variable b* of greater than or equal to 6, with a b*/absolute value of a* ratio of greater than 1.2 according to the selection test described below.

Selection Test

The composition was applied to chestnut-brown keratin fibers, for example the hair, at a rate of 10 grams of composition per 1 gram of chestnut-brown fibers. The composition was spread on so as to cover all of the fibers. The composition was left to act for 20 minutes at room temperature (20 to 25° C.). The fibers were then rinsed with water and then washed with a shampoo based on lauryl ether sulphate. The fibers werethen dried. The spectrocolorimetric characteristics of the fibers were then measured in order to determine the L*a*b* coordinates.

In the CIEL L*a*b* system, a* and b* indicate two color axes: a* indicates the green/red color axis (+a* is red, −a* is green) and b* indicates the blue/yellow color axis (+b* is yellow and −b* is blue); values close to zero for a* and b* correspond to grey shades.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained herein. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope are approximations, the numerical values set forth in the specific examples are reported as precisely as possible. Any numerical value, however, inherently contain certain errors necessarily resulting from the standard deviation found in their respective testing measurements. The following examples are intended to illustrate the invention without limiting the scope as a result.

EXAMPLES

Fluorescent Compound

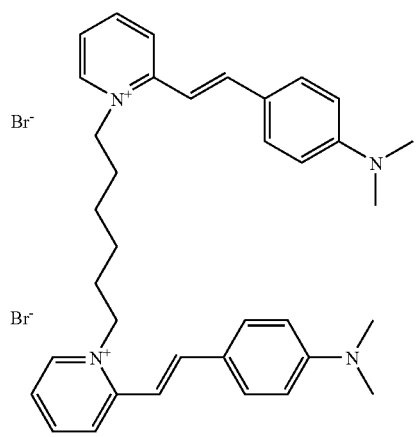

93 g of 2-picoline were reacted with 120 g of 1,6-dibromohexane in dimethylformamide at 110° C. for 5 hours.

The precipitated product was recovered and filtered off.

109 g of the product obtained above were dissolved in methanol and 82.82 g of p-dimethylaminobenzaldehyde were added in two portions, in the presence of pyrrolidine.

The mixture was then left for 30 minutes.

The product was recovered in precipitated form.

Analysis by mass spectroscopy: 266.

Elemental analysis: C, 62.43%; H, 6.40%; Br, 23.07%; N, 8.09%.

The formula was as follows: $C_{36}H_{44}N_4.2Br$.

Compositions

The compositions below were prepared in accordance with the present disclosure:

| Composition | 1 | 2 | 3 |
|---|---|---|---|
| Fluorescent dye | 0.6% | 0.6% | |
| Jaguar HP60 (Rhodia Chimie)(*) | 0.5% | — | |
| Keltrol T (CP Kelco) (**) | — | 0.5% | |
| Blanose 931 M (Aqualon) (***) | — | — | 0.5% |
| Sodium N-cocoylamidoethyl-N-ethoxycarboxymethylglycinate | 2% | 2% | |
| Hexylene glycol | 7% | 7% | |
| Distilled water qs | 100 g | 100 g | |

(*) Hydroxyalkylated nonionic guar gum
(**) Xanthan gum
(***) Carboxymethyl cellulose, sodium salt The percentages are expressed by weight of active material.

Coloration

Each composition was applied to a lock of natural chestnut-brown hair (tone height 4) with a leave-in time of 20 minutes.

The locks were then rinsed and dried under a hood for 30 minutes.

A marked lightening effect was observed on the locks that were treated.

What is claimed is:

1. A cosmetic composition comprising, in a cosmetically acceptable medium, at least one fluorescent dye that is soluble in the medium and at least one non-associative thickening polymer chosen from:
    (i) crosslinked acrylic acid homopolymers;
    (ii) crosslinked 2-acrylamido-2-methylpropanesulphonic acid homopolymers and the partially or totally neutralized acrylamide crosslinked copolymers thereof;
    (iii) ammonium acrylate homopolymers or copolymers of ammonium acrylate and of acrylamide;
    (iv) dimethylaminoethyl methacrylate homopolymers quaternized with methyl chloride; and copolymers of dimethylaminoethyl methacrylate quaternized with methyl chloride and of acrylamide;
    (v) nonionic guar gums;
    (vi) biopolysaccharide gums of microbial origin;
    (vii) gums derived from plant exudates;
    (viii) hydroxypropyl and carboxymethyl celluloses;
    (ix) pectins; and
    (x) alginates;
    wherein the at least one fluorescent dye is chosen from dyes of formula F1 and F3

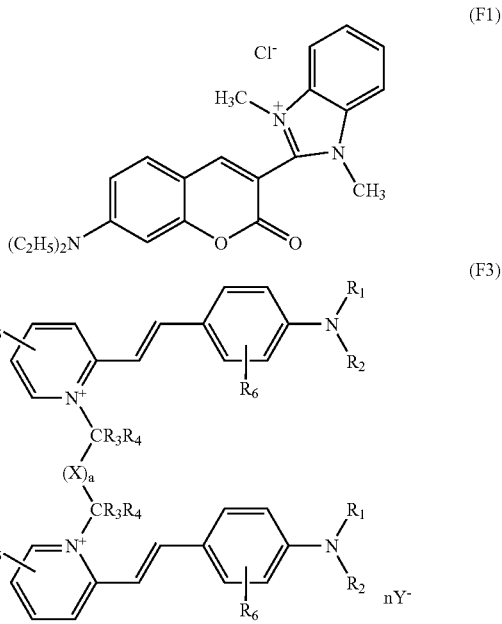

wherein:

$R_1$ and $R_2$, which may be identical or different, are chosen from:
  a hydrogen atom;
  linear or branched alkyl radicals comprising 1 to 10 carbon atoms, optionally interrupted with at least one entity chosen from hetero atoms and groups comprising at least one hetero atom, and/or optionally substituted with at least one entity chosen from hetero atoms, groups comprising at least one hetero atom, and at least one halogen atom; and
  aryl or arylalkyl radicals, the aryl group comprising 6 carbon atoms and the alkyl radical containing 1 to 4 carbon atoms; the aryl radical optionally being substituted with one or more linear or branched alkyl radicals comprising 1 to 4 carbon atoms optionally interrupted with at least one entity chosen from hetero atoms and groups comprising at least one hetero atom, and/or optionally substituted with at least one entity chosen from hetero atoms, groups comprising at least one hetero atom, and at least one halogen atom;

$R_1$ and $R_2$ may optionally be linked so as to form a heterocycle with the nitrogen atom and may comprise one or more other hetero atoms, the heterocycle optionally being substituted with at least one linear or branched alkyl radicals, and optionally being interrupted and optionally substituted with at least one entity chosen from hetero atoms and groups comprising at least one hetero atom and/or substituted with at least one halogen atom; and $R_1$ or $R_2$ may optionally be included in a heterocycle comprising the nitrogen atom and one of the carbon atoms of the phenyl group comprising the nitrogen atom;

$R_3$ and $R_4$, which may be identical or different, are chosen from a hydrogen atom and alkyl radicals comprising 1 to 4 carbon atoms;

R₅, which may be identical or different, is chosen from a hydrogen atom; a halogen atom; and linear or branched alkyl radicals comprising 1 to 4 carbon atoms, optionally interrupted with at least one hetero atom;

R₆, which may be identical or different, is chosen from a hydrogen atom; a halogen atom; linear or branched alkyl radicals comprising 1 to 4 carbon atoms, optionally interrupted with at least one entity chosen from hetero atoms and groups comprising at least one hetero atom, and/or optionally substituted with at least one entity chosen from hetero atoms, groups comprising at least one hetero atom, and at least one halogen atom;

X is chosen from:
  linear or branched alkyl radicals comprising 1 to 14 carbon atoms and alkenyl radicals comprising 2 to 14 carbon atoms, optionally interrupted with at least one entity chosen from hetero atoms and groups comprising at least one hetero atom, and/or optionally substituted with at least one entity chosen from hetero atoms, groups comprising at least one hetero atom, and at least one halogen atom;
  5- or 6-membered heterocyclic radicals optionally substituted with at least one linear or branched alkyl radical comprising 1 to 14 carbon atoms, optionally substituted with at least one hetero atom; with at least one linear or branched aminoalkyl radical comprising 1 to 4 carbon atoms, optionally substituted with at least one hetero atom; with at least one halogen atom;
  fused or non-fused aromatic or diaromatic radicals, optionally separated with an alkyl radical comprising 1 to 4 carbon atoms, the aryl radical(s) optionally being substituted with at least one halogen atom or with at least one alkyl radical comprising 1 to 10 carbon atoms optionally substituted and/or interrupted with at least one hetero atom and/or group bearing at least one hetero atom; and
  dicarbonyl radicals;
  the group X possibly bearing one or more cationic charges;

a being equal to 0 or 1;

Y⁻, which may be identical or different, is chosen from organic and mineral anions; and n is an integer at least equal to 2 and at most equal to the number of cationic charges present in the fluorescent compound;

wherein the composition does not comprise, as the at least one fluorescent dye, 2-[2-(4-dialkylamino)phenylethenyl]-1-alkylpyridinium wherein the alkyl radical of the pyridinium nucleus represents a methyl or ethyl radical, the alkyl radical of the benzene nucleus represents a methyl radical, and wherein the counterion is a halide.

2. The composition of claim 1, wherein the biopolysaccharide gums of microbial origin are chosen from scleroglucan gum and xanthan gum.

3. The composition of claim 1, wherein the gums derived from plant exudates are chosen from gum arabic, ghatti gum, karaya gum, and gum tragacanth.

4. The composition according to claim 1, wherein the nonionic guar gums are modified with $C_1$-$C_6$ hydroxyalkyl groups.

5. The composition of claim 1, wherein the concentration of the at least one non-associative thickening polymer ranges from 0.01% to 10% by weight relative to the total weight of the composition.

6. The composition according to claim 5, wherein the concentration of the at least one non-associative thickening polymer ranges from 0.1% to 5% by weight relative to the total weight of the composition.

7. The composition according to claim 1, wherein the at least one fluorescent dye is soluble in the cosmetically acceptable medium to at least 0.001 g/l at a temperature of between 15 and 25° C.

8. The composition according to claim 1, wherein the at least one fluorescent dye is soluble in the cosmetically acceptable medium to at least 0.5 g/l at a temperature of between 15 and 25° C.

9. The composition according to claim 1, wherein the at least one fluorescent dye is soluble in the cosmetically acceptable medium to at least 1 g/l at a temperature of between 15 and 25° C.

10. The composition according to claim 1, wherein the at least one fluorescent dye is soluble in the cosmetically acceptable medium to at least 5 g/l at a temperature of between 15 and 25° C.

11. The composition according to claim 1, wherein the at least one fluorescent dye is a dye in the orange range.

12. The composition according to claim 1, wherein the at least one fluorescent dye leads to a reflectance maximum that is in the wavelength range from 500 to 650 nanometers.

13. The composition according to claim 12, wherein the at least one fluorescent dye leads to a reflectance maximum that is in the wavelength range from 550 to 620 nanometers.

14. The composition according to claim 1, wherein the at least one fluorescent dye is chosen from the fluorescent dyes belonging to the following families: naphthalimides; cationic and non-cationic coumarins; xanthenodiquinolizines; azaxanthenes; naphtholactams; azlactones; oxazines; thiazines; dioxazines; polycationic fluorescent dyes of azo, azomethine, and methine type.

15. The composition according to claim 1, wherein $R_1$ and $R_2$, which may be identical or different, are chosen from linear or branched alkyl radicals comprising 1 to 4 carbon atoms, optionally interrupted with at least one entity chosen from hetero atoms and groups comprising at least one hetero atom, and/or optionally substituted with at least one entity chosen from hetero atoms, groups comprising at least one hetero atom, and at least one halogen atom.

16. The composition according to claim 1, wherein $R_1$ and $R_2$ may optionally be linked so as to form a heterocycle with the nitrogen atom and may comprise one or more other hetero atoms, the heterocycle optionally being substituted with at least one linear or branched alkyl radical comprising from 1 to 4 carbon atoms, and optionally interrupted with at least one entity chosen from hetero atoms and groups comprising at least one hetero atom, and/or optionally substituted with at least one entity chosen from hetero atoms, groups comprising at least one hetero atom, and at least one halogen atom.

17. The composition according to claim 1, wherein the at least one fluorescent dye is present in an amount ranging from 0.01% to 20% by weight relative to the total weight of the composition.

18. The composition according to claim 17, wherein the at least one fluorescent dye is present in an amount ranging from 0.05% to 10% by weight relative to the total weight of the composition.

19. The composition according to claim 18, wherein the at least one fluorescent dye is present in an amount ranging from 0.1% to 5% by weight relative to the total weight of the composition.

20. The composition according to claim 1, further comprising at least one additional non-fluorescent direct dye chosen from non-fluorescent direct dyes of nonionic, cationic, and anionic nature.

21. The composition according to claim 19, wherein the at least one additional non-fluorescent direct dye is chosen from nitrobenzene dyes, azo dyes, anthraquinone dyes, naphthoquinone dyes, benzoquinone dyes, indigoid dyes, and triaryl-methane-based dyes.

22. The composition according to claim 19, wherein the at least one additional non-fluorescent direct dye is present in an amount ranging from 0.0005% to 12% by weight relative to the total weight of the composition.

23. The composition according to claim 22, wherein the at least one additional non-fluorescent direct dye is present in an amount ranging from 0.005% to 6% by weight relative to the total weight of the composition.

24. The composition according to claim 1, wherein the composition is in the form of a lightening dyeing shampoo.

25. The composition according to claim 1, further comprising at least one oxidation base chosen from para-phenylenediamines, bis(phenyl)alkylenediamines, para-aminophenols, ortho-aminophenols and heterocyclic bases, and the addition salts thereof with an acid or with an alkaline agent.

26. The composition according to claim 25, wherein the at least one oxidation base is present in an amount ranging from 0.0005% to 12% by weight relative to the total weight of the composition.

27. The composition according to claim 26 wherein the at least one oxidation base is present in an amount ranging from 0.005% to 6% by weight relative to the total weight of the composition.

28. The composition according to claim 25, further comprising at least one coupler chosen from meta-phenylenediamines, meta-aminophenols, meta-diphenols and heterocyclic couplers, and the addition salts thereof with an acid or with an alkaline agent.

29. The composition according to claim 28, wherein the at least one coupleris present in an amount ranging from 0.0001% to 10% by weight relative to the total weight of the dye composition.

30. The composition according to claim 29, wherein the at least one coupler is present in an amount ranging from 0.005% to 5% by weight relative to the total weight of the dye composition.

31. The composition according to claim 1, further comprising at least one oxidizing agent.

32. The composition according to claim 31, wherein the at least one oxidizing agent is chosen from hydrogen peroxide, urea peroxide, alkali metal bromates, persalts, and enzymes.

33. The composition of claim 32, wherein the persalts are chosen from perborates and persulphates.

34. The composition of claim 32, wherein the enzymes are chosen such as peroxidases and two-electron or four-electron oxidoreductases 35. A process for dyeing human keratin fibers with a lightening effect, comprising:
  a) applying to the human keratin fibers for a time sufficient to develop the desired coloration and lightening, a composition comprising, in a cosmetically acceptable medium, at least one fluorescent dye that is soluble in the medium and at least one non-associative thickening polymer chosen from:
    (i) crosslinked acrylic acid homopolymers;
    (ii) crosslinked 2-acrylamido-2-methylpropanesulphonic acid homopolymers and the partially or totally neutralized acrylamide crosslinked copolymers thereof;
    (iii) ammonium acrylate homopolymers or copolymers of ammonium acrylate and of acrylamide;
    (iv) dimethylaminoethyl methacrylate homopolymers quaternized with methyl chloride; and copolymers of dimethylaminoethyl methacrylate quaternized with methyl chloride and of acrylamide;
    (v) nonionic guar gums;
    (vi) biopolysaccharide gums of microbial origin;
    (vii) gums derived from plant exudates;
    (viii) hydroxypropyl and carboxymethyl celluloses;
    (ix) pectins; and
    (x) alginates,
  wherein the at least one fluorescent dye is chosen from dyes of formula F1 and F3 wherein:

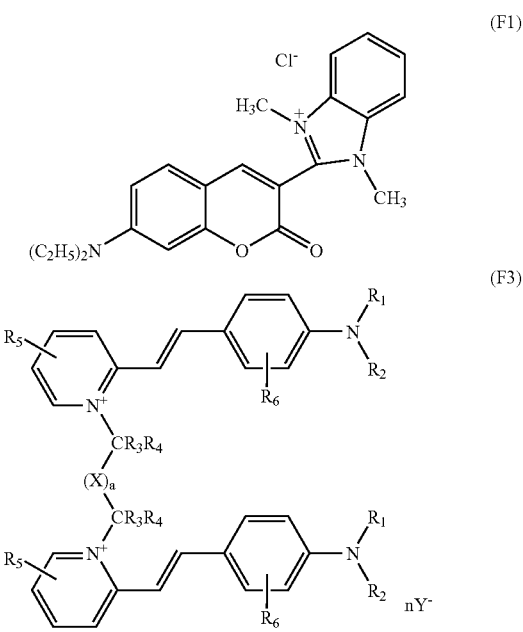

$R_1$ and $R_2$, which may be identical or different, are chosen from:
  a hydrogen atom;
  linear or branched alkyl radicals comprising 1 to 10 carbon atoms, optionally interrupted with at least one entity chosen from hetero atoms and groups comprising at least one hetero atom, and/or optionally substituted with at least one entity chosen from hetero atoms, groups comprising at least one hetero atom, and at least one halogen atom; and
  aryl or arylalkyl radicals, the aryl group comprising 6 carbon atoms and the alkyl radical containing 1 to 4 carbon atoms; the aryl radical optionally being substituted with one or more linear or branched alkyl radicals comprising 1 to 4 carbon atoms optionally interrupted with at least one entity chosen from hetero atoms and groups comprising at least one hetero atom, and/or optionally substituted with at least one entity chosen from hetero atoms, groups comprising at least one hetero atom, and at least one halogen atom;

$R_1$ and $R_2$ may optionally be linked so as to form a heterocycle with the nitrogen atom and may comprise one or more other hetero atoms, the heterocycle optionally being substituted with at least one linear or branched alkyl radicals, and optionally being interrupted and optionally substituted with at least one entity chosen from hetero atoms and groups comprising at least one hetero atom and/or substituted with at least one halogen atom; and $R_1$ or $R_2$ may optionally be included in a heterocycle comprising the nitrogen atom and one of the carbon atoms of the phenyl group comprising the nitrogen atom;

$R_3$ and $R_4$, which may be identical or different, are chosen from a hydrogen atom and alkyl radicals comprising 1 to 4 carbon atoms;

$R_5$, which may be identical or different, is chosen from a hydrogen atom; a halogen atom; and linear or branched alkyl radicals comprising 1 to 4 carbon atoms, optionally interrupted with at least one hetero atom;

$R_6$, which may be identical or different, is chosen from a hydrogen atom; a halogen atom; linear or branched alkyl radicals comprising 1 to 4 carbon atoms, optionally interrupted with at least one entity chosen from hetero atoms and groups comprising at least one hetero atom, and/or optionally substituted with at least one entity chosen from hetero atoms, groups comprising at least one hetero atom, and at least one halogen atom;

X is chosen from:
  linear or branched alkyl radicals comprising 1 to 14 carbon atoms and alkenyl radicals comprising 2 to 14 carbon atoms, optionally interrupted with at least one entity chosen from hetero atoms and groups comprising at least one hetero atom, and/or optionally substituted with at least one entity chosen from hetero atoms, groups comprising at least one hetero atom, and at least one halogen atom;
  5- or 6-membered heterocyclic radicals optionally substituted with at least one linear or branched alkyl radical comprising 1 to 14 carbon atoms, optionally substituted with at least one hetero atom; with at least one linear or branched aminoalkyl radical comprising 1 to 4 carbon atoms, optionally substituted with at least one hetero atom; with at least one halogen atom;
  fused or non-fused aromatic or diaromatic radicals, optionally separated with an alkyl radical comprising 1 to 4 carbon atoms, the aryl radical(s) optionally being substituted with at least one halogen atom or with at least one alkyl radical comprising 1 to 10 carbon atoms optionally substituted and/or interrupted with at least one hetero atom and/or group bearing at least one hetero atom; and
  dicarbonyl radicals;
  the group X possibly bearing one or more cationic charges;

a being equal to 0 or 1;

$Y^-$, which may be identical or different, is chosen from organic and mineral anions; and n is an integer at least equal to 2 and at most equal to the number of cationic charges present in the fluorescent compound;

wherein the composition does not comprise, as the at least one fluorescent dye, 2-[2-(4-dialkylamino)phenylethenyl]-1-alkylpyridinium, wherein the alkyl radical of the pyridinium nucleus represents a methyl or ethyl radical, the alkyl radical of the benzene nucleus represents a methyl radical, and wherein the counterion is a halide, b) optionally rinsing the human keratin fibers;

c) optionally washing the human keratin fibers with shampoo and rinsing; and d) drying the human keratin fibers.

36. The process of claim 35, wherein the biopolysaccharide gums of microbial origin are chosen from scleroglucan gum and xanthan gum.

37. The process of claim 35, wherein the gums derived from plant exudates are chosen from gum arabic, ghatti gum, karaya gum, and gum tragacanth.

38. The process according to claim 35, comprising before applying said composition to the human keratin fibers, separately storing, said composition, and a second composition comprising, in a cosmetically acceptable medium, at least one oxidizing agent, and then mixing them together at the time of use.

39. The process according to claim 35, wherein the composition is applied to hair with a tone height of less than or equal to 6.

40. The process according to claim 35, wherein the composition is applied to hair with a tone height of less than or equal to 4.

41. The process according to claim 35, wherein the keratin fibers are artificially colored or pigmented.

42. A process for coloring dark skin with a lightening effect, comprising:

(a) applying to the skin a composition comprising, in a cosmetically acceptable medium, at least one fluorescent dye that is soluble in the medium and at least one non-associative thickening polymer chosen from:
  (i) crosslinked acrylic acid homopolymers;
  (ii) crosslinked 2-acrylamido-2-methylpropanesulphonic acid homopolymers and the partially or totally neutralized acrylamide crosslinked copolymers thereof;
  (iii) ammonium acrylate homopolymers or copolymers of ammonium acrylate and of acrylamide;
  (iv) dimethylaminoethyl methacrylate homopolymers quaternized with methyl chloride; and copolymers of dimethylaminoethyl methacrylate quaternized with methyl chloride and of acrylamide;
  (v) nonionic guar gums;
  (vi) biopolysaccharide gums of microbial origin;
  (vii) gums derived from plant exudates;
  (viii) hydroxypropyl or carboxymethyl celluloses;
  (ix) pectins; and
  (x) alginates, wherein the at least one fluorescent dye is chosen from dyes of formula F1 and F3 wherein:

(F1)

[Chemical structure: a coumarin derivative with Cl− counterion, containing a fused benzimidazolium ring system with $H_3C-N^+$ and $N-CH_3$ groups, attached to a coumarin bearing a $(C_2H_5)_2$N substituent]

-continued

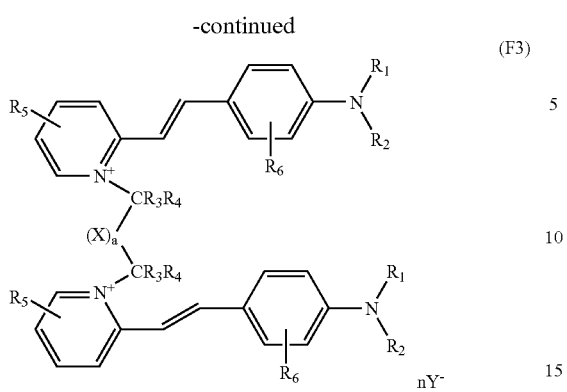

(F3)

R₁ and R₂, which may be identical or different, are chosen from:
a hydrogen atom;
linear or branched alkyl radicals comprising 1 to 10 carbon atoms, optionally interrupted with at least one entity chosen from hetero atoms and groups comprising at least one hetero atom, and/or optionally substituted with at least one entity chosen from hetero atoms, groups comprising at least one hetero atom, and at least one halogen atom; and
aryl or arylalkyl radicals, the aryl group comprising 6 carbon atoms and the alkyl radical containing 1 to 4 carbon atoms; the aryl radical optionally being substituted with one or more linear or branched alkyl radicals comprising 1 to 4 carbon atoms optionally interrupted with at least one entity chosen from hetero atoms and groups comprising at least one hetero atom, and/or optionally substituted with at least one entity chosen from hetero atoms, groups comprising at least one hetero atom, and at least one halogen atom;
R₁ and R₂ may optionally be linked so as to form a heterocycle with the nitrogen atom and may comprise one or more other hetero atoms, the heterocycle optionally being substituted with at least one linear or branched alkyl radicals, and optionally being interrupted and optionally substituted with at least one entity chosen from hetero atoms and groups comprising at least one hetero atom and/or substituted with at least one halogen atom; and
R₁ or R₂ may optionally be included in a heterocycle comprising the nitrogen atom and one of the carbon atoms of the phenyl group comprising the nitrogen atom;
R₃ and R₄, which may be identical or different, are chosen from a hydrogen atom and alkyl radicals comprising 1 to 4 carbon atoms;
R₅, which may be identical or different, is chosen from a hydrogen atom; a halogen atom; and linear or branched alkyl radicals comprising 1 to 4 carbon atoms, optionally interrupted with at least one hetero atom;
R₆, which may be identical or different, is chosen from a hydrogen atom; a halogen atom; linear or branched alkyl radicals comprising 1 to 4 carbon atoms, optionally interrupted with at least one entity chosen from hetero atoms and groups comprising at least one hetero atom, and/or optionally substituted with at least one entity chosen from hetero atoms, groups comprising at least one hetero atom, and at least one halogen atom;

X is chosen from:
linear or branched alkyl radicals comprising 1 to 14 carbon atoms and alkenyl radicals comprising 2 to 14 carbon atoms, optionally interrupted with at least one entity chosen from hetero atoms and groups comprising at least one hetero atom, and/or optionally substituted with at least one entity chosen from hetero atoms, groups comprising at least one hetero atom, and at least one halogen atom;
5- or 6-membered heterocyclic radicals optionally substituted with at least one linear or branched alkyl radical comprising 1 to 14 carbon atoms, optionally substituted with at least one hetero atom; with at least one linear or branched aminoalkyl radical comprising 1 to 4 carbon atoms, optionally substituted with at least one hetero atom; with at least one halogen atom;
fused or non-fused aromatic or diaromatic radicals, optionally separated with an alkyl radical comprising 1 to 4 carbon atoms, the aryl radical(s) optionally being substituted with at least one halogen atom or with at least one alkyl radical comprising 1 to 10 carbon atoms optionally substituted and/or interrupted with at least one hetero atom and/or group bearing at least one hetero atom; and
dicarbonyl radicals;
the group X possibly bearing one or more cationic charges;
a being equal to 0 or 1;
Y⁻, which may be identical or different, is chosen from organic and mineral anions; and
n is an integer at least equal to 2 and at most equal to the number of cationic charges present in the fluorescent compound;
wherein the composition does not comprise, as the at least one fluorescent dye 2-[2-(4-dialkylamino)phenylethenyl]-1-alkylpyridinium wherein the alkyl radical of the pyridinium nucleus represents a methyl or ethyl radical, the alkyl radical of the benzene nucleus represents a methyl radical, and wherein the counterion is a halide,
(b) drying the skin.
43. The process of claim 42, wherein the biopolysaccharide gums of microbial origin are chosen from scleroglucan gum and xanthan gum.
44. The process of claim 42, wherein the gums derived from plant exudates are chosen from gum arabic, ghatti gum, karaya gum and gum tragacanth.
45. A multi-compartment device for dyeing with a lightening effect, comprising:
(a) at least one compartment containing a composition comprising, in a cosmetically acceptable medium, at least one fluorescent dye that is soluble in said medium and at least one non-associative thickening polymer chosen from:
(i) crosslinked acrylic acid homopolymers;
(ii) crosslinked 2-acrylamido-2-methylpropanesulphonic acid homopolymers and the partially or totally neutralized acrylamide crosslinked copolymers thereof;
(iii) ammonium acrylate homopolymers or copolymers of ammonium acrylate and of acrylamide;
(iv) dimethylaminoethyl methacrylate homopolymers quaternized with methyl chloride; and copolymers of dimethylaminoethyl methacrylate quaternized with methyl chloride and of acrylamide;

(v) nonionic guar gums;
(vi) biopolysaccharide gums of microbial origin;
(vii) gums derived from plant exudates;
(viii) hydroxypropyl or carboxymethyl celluloses;
(ix) pectins; and
(x) alginates,

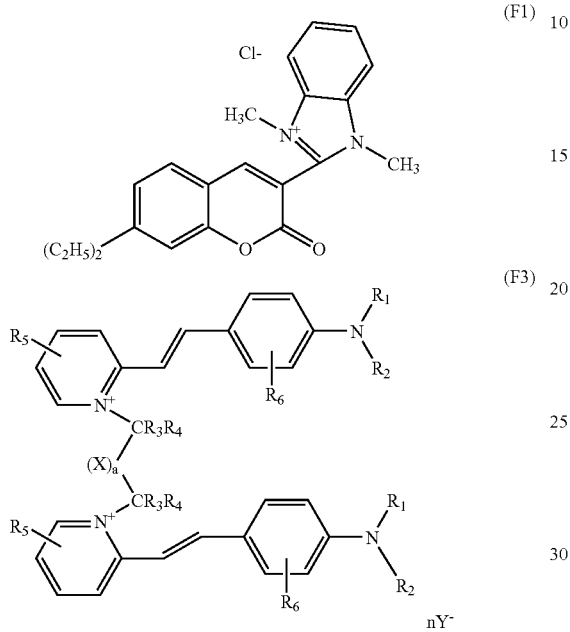

wherein the at least one fluorescent dye is chosen from dyes of formula F1 and F3 wherein:

$R_1$ and $R_2$, which may be identical or different, are chosen from;
  a hydrogen atom;
  linear or branched alkyl radicals comprising 1 to 10 carbon atoms, optionally interrupted with at least one entity chosen from hetero atoms and groups comprising at least one hetero atom, and/or optionally substituted with at least one entity chosen from hetero atoms, groups comprising at least one hetero atom, and at least one halogen atom; and
  aryl or arylalkyl radicals, the aryl group comprising 6 carbon atoms and the alkyl radical containing 1 to 4 carbon atoms; the aryl radical optionally being substituted with one or more linear or branched alkyl radicals comprising 1 to 4 carbon atoms optionally interrupted with at least one entity chosen from hetero atoms and groups comprising at least one hetero atom, and/or optionally substituted with at least one entity chosen from hetero atoms, groups comprising at least one hetero atom, and at least one halogen atom;
$R_1$ and $R_2$ may optionally be linked so as to form a heterocycle with the nitrogen atom and may comprise one or more other hetero atoms, the heterocycle optionally being substituted with at least one linear or branched alkyl radicals, and optionally being interrupted and optionally substituted with at least one entity chosen from hetero atoms and groups comprising at least one hetero atom and/or substituted with at least one halogen atom; and $R_1$ or $R_2$ may optionally be included in a heterocycle comprising the nitrogen atom and one of the carbon atoms of the phenyl group comprising the nitrogen atom;
$R_3$ and $R_4$, which may be identical or different, are chosen from a hydrogen atom and alkyl radicals comprising 1 to 4 carbon atoms;
$R_5$, which may be identical or different, is chosen from a hydrogen atom; a halogen atom; and linear or branched alkyl radicals comprising 1 to 4 carbon atoms, optionally interrupted with at least one hetero atom;
$R_6$, which may be identical or different, is chosen from a hydrogen atom; a halogen atom; linear or branched alkyl radicals comprising 1 to 4 carbon atoms, optionally interrupted with at least one entity chosen from hetero atoms and groups comprising at least one hetero atom, and/or optionally substituted with at least one entity chosen from hetero atoms, groups comprising at least one hetero atom, and at least one halogen atom;
X is chosen from:
  linear or branched alkyl radicals comprising 1 to 14 carbon atoms and alkenyl radicals comprising 2 to 14 carbon atoms, optionally interrupted with at least one entity chosen from hetero atoms and groups comprising at least one hetero atom, and/or optionally substituted with at least one entity chosen from hetero atoms, groups comprising at least one hetero atom, and at least one halogen atom;
  5- or 6-membered heterocyclic radicals optionally substituted with at least one linear or branched alkyl radical comprising 1 to 14 carbon atoms, optionally substituted with at least one hetero atom; with at least one linear or branched aminoalkyl radical comprising 1 to 4 carbon atoms, optionally substituted with at least one hetero atom; with at least one halogen atom;
  fused or non-fused aromatic or diaromatic radicals, optionally separated with an alkyl radical comprising 1 to 4 carbon atoms, the aryl radical(s) optionally being substituted with at least one halogen atom or with at least one alkyl radical comprising 1 to 10 carbon atoms optionally substituted and/or interrupted with at least one hetero atom and/or group bearing at least one hetero atom; and
  dicarbonyl radicals;
  the group X possibly bearing one or more cationic charges;
a being equal to 0 or 1;
$Y^-$, which may be identical or different, is chosen from organic and mineral anions; and
  n is an integer at least equal to 2 and at most equal to the number of cationic charges present in the fluorescent compound;
  wherein the composition does not comprise, as the at least one fluorescent dye 2-[2-(4-dialkylamino)phenylethenyl]-1-alkylpyridinium wherein the alkyl radical of the pyridinium nucleus represents a methyl or ethyl radical, the alkyl radical of the benzene nucleus represents a methyl radical and wherein the counterion is a halide; and
(b) at least one compartment containing a composition comprising at least one oxidizing agent.

46. The process of claim 45, wherein the biopolysaccharide gums of microbial origin are chosen from scleroglucan gum and xanthan gum.

47. The process of claim 45, wherein the gums derived from plant exudates are chosen from gum arabic, ghatti gum, karaya gum, and gum tragacanth.

48. A method for dyeing human keratin materials with a lightening effect, with a composition comprising, in a cosmetically acceptable medium, at least one fluorescent dye that is soluble in said medium and at least one non-associative thickening polymer chosen from:
(i) crosslinked acrylic acid homopolymers;
(ii) crosslinked 2-acrylamido-2-methylpropanesulphonic acid homopolymers and the partially or totally neutralized acrylamide crosslinked copolymers thereof;
(iii) ammonium acrylate homopolymers or copolymers of ammonium acrylate and of acrylamide;
(iv) dimethylaminoethyl methacrylate homopolymers quaternized with methyl chloride; and copolymers of dimethylaminoethyl methacrylate quaternized with methyl chloride and of acrylamide;
(v) nonionic guar gums;
(vi) biopolysaccharide gums of microbial origin;
(vii) gums derived from plant exudates;
(viii) hydroxypropyl or carboxymethyl celluloses;
(ix) pectins; and
(x) alginates,
wherein the at least one fluorescent dye is chosen from dyes of formula F1 and F3 wherein:

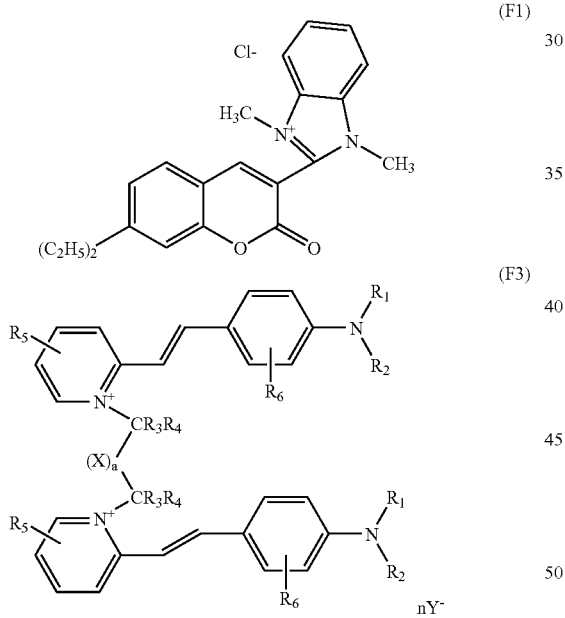

$R_1$ and $R_2$, which may be identical or different, are chosen from:
a hydrogen atom;
linear or branched alkyl radicals comprising 1 to 10 carbon atoms, optionally interrupted with at least one entity chosen from hetero atoms and groups comprising at least one hetero atom, and/or optionally substituted with at least one entity chosen from hetero atoms, groups comprising at least one hetero atom, and at least one halogen atom; and
aryl or arylalkyl radicals, the aryl group comprising 6 carbon atoms and the alkyl radical containing 1 to 4 carbon atoms; the aryl radical optionally being substituted with one or more linear or branched alkyl radicals comprising 1 to 4 carbon atoms optionally interrupted with at least one entity chosen from hetero atoms and groups comprising at least one hetero atom, and/or optionally substituted with at least one entity chosen from hetero atoms, groups comprising at least one hetero atom, and at least one halogen atom;

$R_1$ and $R_2$ may optionally be linked so as to form a heterocycle with the nitrogen atom and may comprise one or more other hetero atoms, the heterocycle optionally being substituted with at least one linear or branched alkyl radicals, and optionally being interrupted and optionally substituted with at least one entity chosen from hetero atoms and groups comprising at least one hetero atom and/or substituted with at least one halogen atom; and $R_1$ or $R_2$ may optionally be included in a heterocycle comprising the nitrogen atom and one of the carbon atoms of the phenyl group comprising the nitrogen atom;

$R_3$ and $R_4$, which may be identical or different, are chosen from a hydrogen atom and alkyl radicals comprising 1 to 4 carbon atoms;

$R_5$, which may be identical or different, is chosen from a hydrogen atom; a halogen atom; and linear or branched alkyl radicals comprising 1 to 4 carbon atoms, optionally interrupted with at least one hetero atom;

$R_6$, which may be identical or different, is chosen from a hydrogen atom; a halogen atom; linear or branched alkyl radicals comprising 1 to 4 carbon atoms, optionally interrupted with at least one entity chosen from hetero atoms and groups comprising at least one hetero atom, and/or optionally substituted with at least one entity chosen from hetero atoms, groups comprising at least one hetero atom, and at least one halogen atom;

X is chosen from:
linear or branched alkyl radicals comprising 1 to 14 carbon atoms and alkenyl radicals comprising 2 to 14 carbon atoms, optionally interrupted with at least one entity chosen from hetero atoms and groups comprising at least one hetero atom, and/or optionally substituted with at least one entity chosen from hetero atoms, groups comprising at least one hetero atom, and at least one halogen atom;
5- or 6-membered heterocyclic radicals optionally substituted with at least one linear or branched alkyl radical comprising 1 to 14 carbon atoms, optionally substituted with at least one hetero atom; with at least one linear or branched aminoalkyl radical comprising 1 to 4 carbon atoms, optionally substituted with at least one hetero atom; with at least one halogen atom;
fused or non-fused aromatic or diaromatic radicals, optionally separated with an alkyl radical comprising 1 to 4 carbon atoms, the aryl radical(s) optionally being substituted with at least one halogen atom or with at least one alkyl radical comprising 1 to 10 carbon atoms optionally substituted and/or interrupted with at least one hetero atom and/or group bearing at least one hetero atom; and
dicarbonyl radicals;
the group X possibly bearing one or more cationic charges;
a being equal to 0 or 1;
$Y^-$, which may be identical or different, is chosen from organic and mineral anions; and n is an integer at least equal to 2 and at most equal to the number of cationic charges present in the fluorescent compound;

wherein the composition does not comprise, as the at least one fluorescent dye, 2-[2-(4-dialkylamino)phenylethenyl]-1-alkylpyridinium wherein the alkyl radical of the pyridinium nucleus represents a methyl or ethyl radical, the alkyl radical of the benzene nucleus represents a methyl radical and wherein the counterion is a halide.

49. The process of claim 48, wherein the biopolysaccharide gums of microbial origin are chosen from scleroglucan gum and xanthan gum.

50. The process of claim 48, wherein the gums derived from plant exudates are chosen from gum arabic, ghatti gum, karaya gum, and gum tragacanth.

51. A method according to claim 48, wherein the fluorescent dye is a dye in the orange range.

52. A method according to claim 48, wherein the at least one fluorescent dye leads to a reflectance maximum that is in the wavelength range from 500 to 650 nanometers.

53. A method according to claim 52, wherein the at least one fluorescent dye leads to a reflectance maximum that is in the wavelength range from 550 to 620 nanometers.

54. A method according to claim 48, wherein the at least one fluorescent dye is chosen from the fluorescent dyes of the following families: naphthalimides; cationic and non-cationic coumarins; xanthenodiquinolizines; azaxanthenes; naphtholactams; azlactones; oxazines; thiazines; dioxazines; monocationic and polycationic fluorescent dyes of azo, azomethine and methine type.

55. A method according to claim 48, wherein the at least one fluorescent dye is present in an amount ranging from 0.01% to 20% by weight, relative to the total weight of the composition.

56. A method according to claim 55, wherein the at least one fluorescent dye is present in an amount ranging from 0.05% to 10% by weight relative to the total weight of the composition.

57. A method according to claim 56, wherein the at least one fluorescent dye is present in an amount ranging from 0.1% to 5% by weight relative to the total weight of the composition.

58. A method according to claim 48, wherein the keratin materials are artificially colored or pigmented keratin fibers.

59. A method according to claim 48, wherein the keratin materials are hair.

60. A method according to claim 48, wherein the keratin materials are dark skin.

61. A method according to claim 48, wherein the hair has a tone height of less than or equal to 6.

62. A method according to claim 48, wherein the hair has a tone height of less than or equal to 4.

* * * * *

UNITED STATES PATENT AND TRADEMARK OFFICE
CERTIFICATE OF CORRECTION

PATENT NO.       : 7,250,064 B2
APPLICATION NO.  : 10/814236
DATED            : July 31, 2007
INVENTOR(S)      : Grégory Plos et al.

It is certified that error appears in the above-identified patent and that said Letters Patent is hereby corrected as shown below:

In claim 1, column 26, lines 1-12, " 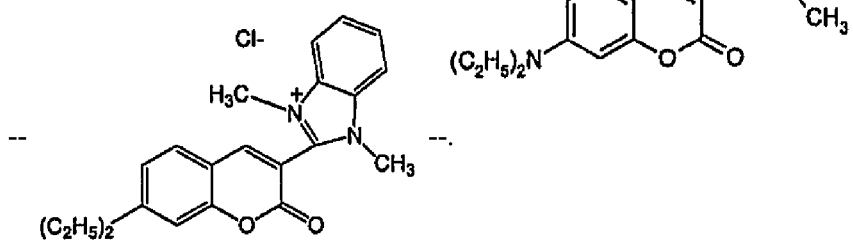 " should read -- 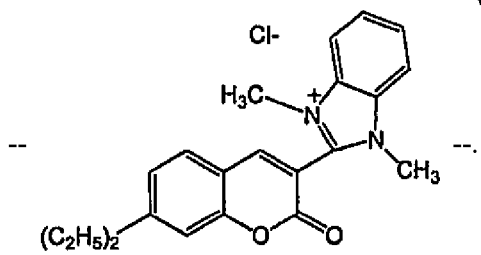 --.

In claim 1, column 26, line 56, "radicals," should read --radical,--.

In claim 21, column 29, line 5, "claim 19," should read --claim 20,--.

In claim 21, column 29, line 9, "triaryl-methane-based" should read --triarylmethane-based--.

In claim 22, column 29, line 10, "claim 19," should read --claim 20,--.

In claim 29, column 29, line 41, "coupleris" should read --coupler is--.

In claim 35, column 30, line 19, delete "wherein:".

In claim 35, column 30, lines 22-31, "  " should read -- 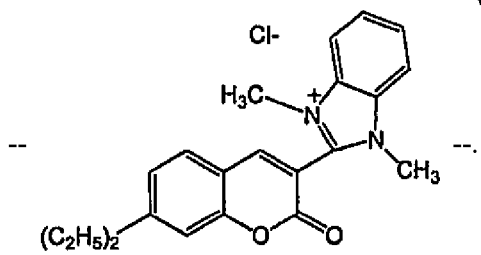 --.

In claim 35, column 30, line 46, following formula "(F3)" insert --wherein:--.

UNITED STATES PATENT AND TRADEMARK OFFICE
CERTIFICATE OF CORRECTION

PATENT NO. : 7,250,064 B2
APPLICATION NO. : 10/814236
DATED : July 31, 2007
INVENTOR(S) : Grégory Plos et al.

It is certified that error appears in the above-identified patent and that said Letters Patent is hereby corrected as shown below:

In claim 35, column 31, line 5, "radicals," should read --radical,--.

In claim 42, column 32, line 54, delete "wherein:".

In claim 42, column 33, line 17, following formula "(F3)" insert --wherein:--.

In claim 42, column 33, line 43, "radicals," should read --radical,--.

In claim 42, column 34, line 42, after "halide," insert --and--.

In claim 45, column 35, lines 9-33, delete formulas "(F1)" and "(F3)" in their entirety.

In claim 45, column 35, line 36, after "F3" and before "wherein:" insert

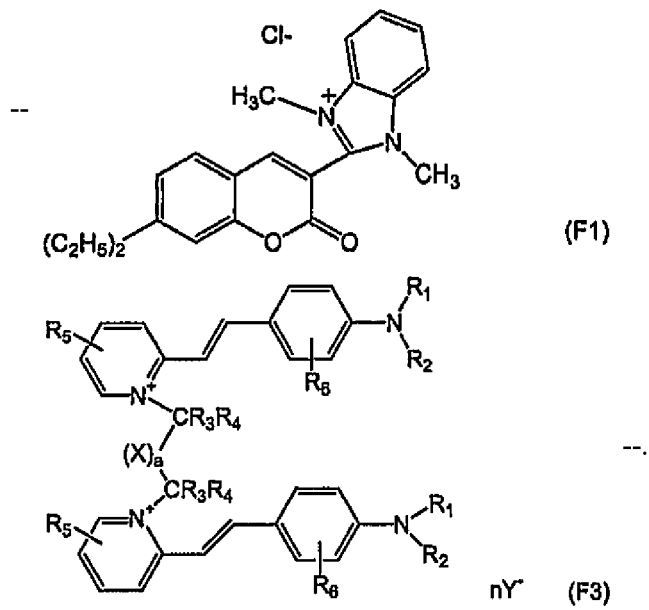

In claim 45, column 35, line 38, "from;" should read --from:--.

In claim 45, column 35, line 63, "radicals," should read --radical,--.

In claim 48, column 37, line 26, delete "wherein:".

In claim 48, column 37, line 53, following formula (F3) insert --wherein:--.

UNITED STATES PATENT AND TRADEMARK OFFICE
CERTIFICATE OF CORRECTION

PATENT NO. : 7,250,064 B2
APPLICATION NO. : 10/814236
DATED : July 31, 2007
INVENTOR(S) : Grégory Plos et al.

It is certified that error appears in the above-identified patent and that said Letters Patent is hereby corrected as shown below:

In claim 48, column 38, line 12, "radicals," should read --radical,--.

Signed and Sealed this

Eleventh Day of December, 2007

JON W. DUDAS
*Director of the United States Patent and Trademark Office*